United States Patent
Ben-Haim et al.

(10) Patent No.: US 6,690,963 B2
(45) Date of Patent: Feb. 10, 2004

(54) SYSTEM FOR DETERMINING THE LOCATION AND ORIENTATION OF AN INVASIVE MEDICAL INSTRUMENT

(75) Inventors: Shlomo Ben-Haim, Haifa (IL); Daniel Osadchy, Haifa (IL); Udi Peless, Even-Yehuda (IL); Ilan Greenberg, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 08/793,371

(22) PCT Filed: Jan. 24, 1995

(86) PCT No.: PCT/US95/01103

§ 371 (c)(1),
(2), (4) Date: May 14, 1997

(87) PCT Pub. No.: WO96/05768

PCT Pub. Date: Feb. 29, 1996

(65) Prior Publication Data

US 2002/0065455 A1 May 30, 2002

(51) Int. Cl.[7] .................................................. A61B 5/05
(52) U.S. Cl. ...................... 600/424; 600/117; 600/437; 607/99; 606/41
(58) Field of Search .................................. 600/424, 407, 600/117, 437; 324/207.1, 207.13, 207.17, 207.26; 606/130, 41; 128/899; 607/96–99

(56) References Cited

U.S. PATENT DOCUMENTS

| | | |
|---|---|---|
| 3,644,825 A | 2/1972 | Davis, Jr. et al. |
| 3,868,565 A | 2/1975 | Kuipers |
| 4,017,858 A | 4/1977 | Kuipers |

(List continued on next page.)

FOREIGN PATENT DOCUMENTS

| | | |
|---|---|---|
| DE | 4238176 | 5/1994 |
| EP | 0038151 | 10/1981 |
| EP | 0399536 | 11/1990 |
| EP | 567187 | 6/1993 |
| GB | 2094590 | 9/1982 |
| GB | 2155736 | 9/1985 |
| GB | 2197078 | 10/1987 |
| WO | WO 8809515 | 12/1988 |
| WO | WO 94/03227 | 2/1994 |
| WO | WO 9404938 | 3/1994 |
| WO | WO 9509562 | 4/1995 |

OTHER PUBLICATIONS

Breyer et al., Ultrasonically Marked Catheter, A Method for Positive Ecographic Catheter Position and Identification, *Medical and Biological Engineering and Computing*, May 1985, pp. 268–271.

Remmel, An Inexpensive Eye Movement Monitor Using the Scleral Search Coil Technique, *IEEE Transactions on Biomedical Engineering*, vol. BME–31, No. 4, Apr. 1984, pp. 388–390.

*Primary Examiner*—Ruth S. Smith
(74) *Attorney, Agent, or Firm*—Louis J. Capezzuto

(57) ABSTRACT

A locating system for determining the location and orientation of an invasive medical instrument, for example a catheter (10) or endoscope, relative to a reference frame, comprising: a plurality of field generators (18, 20, 22) which generate known, distinguishable fields, preferably continuous AC magnetic fields, in response to drive signals; a plurality of sensors (30, 32, 34) situated in the invasive medical instrument (10) proximate the distal end thereof which generate sensor signals in response to said fields; and a signal processor (26) which has an input for a plurality of signals corresponding to said drive signals and said sensor signals and which produces the three location coordinates and three orientation coordinates of a point on the invasive medical instrument.

28 Claims, 19 Drawing Sheets

U.S. PATENT DOCUMENTS

| | | |
|---|---|---|
| 4,054,881 A | 10/1977 | Raab |
| 4,173,228 A | 11/1979 | Van Steenwyk et al. |
| 4,223,228 A | 9/1980 | Kaplan |
| 4,317,078 A | 2/1982 | Weed et al. |
| 4,396,885 A | 8/1983 | Constant |
| 4,422,041 A | 12/1983 | Lineau |
| 4,613,866 A | 9/1986 | Blood |
| 4,642,786 A | 2/1987 | Hansen |
| 4,652,820 A | 3/1987 | Maresca |
| 4,661,773 A | 4/1987 | Kawakita et al. |
| 4,697,595 A | 10/1987 | Breyer et al. |
| 4,710,708 A | 12/1987 | Rorden et al. |
| 4,771,788 A | 9/1988 | Millar |
| 4,821,731 A * | 4/1989 | Martinelli et al. .......... 600/439 |
| 4,829,250 A | 5/1989 | Rotier |
| 4,849,692 A | 7/1989 | Blood |
| 4,945,305 A | 7/1990 | Blood |
| 5,042,486 A | 8/1991 | Pfeiler et al. |
| 5,047,715 A | 9/1991 | Morgenstern |
| 5,056,517 A | 10/1991 | Fenici |
| 5,062,151 A | 10/1991 | Shipley |
| 5,070,462 A | 12/1991 | Chau |
| 5,109,194 A | 4/1992 | Cantaloube |
| 5,117,181 A | 5/1992 | Clergeot et al. |
| 5,168,222 A | 12/1992 | Volsin et al. |
| 5,172,056 A | 12/1992 | Volsin |
| 5,186,174 A | 2/1993 | Schlondorff et al. |
| 5,211,165 A | 5/1993 | Dumoulin et al. |
| 5,218,174 A | 6/1993 | Gray et al. |
| 5,231,989 A | 8/1993 | Middleman et al. |
| 5,253,647 A * | 10/1993 | Takahashi et al. .......... 600/424 |
| 5,255,684 A | 10/1993 | Rello |
| 5,273,025 A * | 12/1993 | Sakiyama et al. .......... 128/899 |
| 5,276,430 A | 1/1994 | Granovsky |
| 5,295,484 A * | 3/1994 | Marcus et al. .............. 600/439 |
| 5,295,486 A | 3/1994 | Wollschläger et al. |
| 5,318,025 A * | 6/1994 | Dumoulin et al. .......... 600/424 |
| 5,341,807 A | 8/1994 | Nardella |
| 5,373,845 A | 12/1994 | Gardineer et al. |
| 5,375,596 A | 12/1994 | Twiss et al. |
| 5,397,304 A | 3/1995 | Truckai |
| 5,425,367 A | 6/1995 | Shapiro et al. |
| 5,429,132 A | 7/1995 | Guy et al. |
| 5,443,489 A * | 8/1995 | Ben-Haim ................. 607/115 |
| 5,558,091 A | 9/1996 | Acker |
| 5,622,170 A * | 4/1997 | Schulz ....................... 600/407 |
| 5,681,260 A * | 10/1997 | Ueda et al. ................. 600/114 |
| 5,727,553 A * | 3/1998 | Saad .......................... 600/407 |
| 5,729,129 A * | 3/1998 | Acker ..................... 324/207.12 |
| 5,752,513 A * | 5/1998 | Acker et al. ................ 600/407 |
| 5,755,725 A * | 5/1998 | Druais ....................... 606/130 |

* cited by examiner

SYSTEM FOR DETERMINING THE LOCATION AND ORIENTATION OF AN INVASIVE MEDICAL INSTRUMENT

FIELD OF THE INVENTION

The present invention relates to medical diagnosis, treatment and imaging systems. More particularly, the present invention relates to medical probes whose location can be detected and adjusted and which have an additional detection, imaging and/or treatment function.

BACKGROUND OF THE INVENTION

Probes, such as catheters, suitable for various medical procedures and internal imaging, are fairly common. Such probes include: balloon angioplasty catheters, catheters with laser-, electrical- or cryo-ablation characteristics, catheters having ultrasound imaging heads, probes used for nearly incisionless-surgery or diagnosis, and endoscopes. Where such probes are used for treatment, the probes must be carefully positioned in relation to the body structure. Even for imaging systems such as ultrasound systems, some positioning capability has been described.

In cardiovascular examinations and in particular in those using invasive techniques, multiple catheters are inserted into the vascular system and then advanced towards the cardiac chambers. The procedure itself is generally performed under fluoroscope guidance which necessitates the use of a continuous source of x-ray as a transillumination source. The image generated using the fluoroscope is a 2D display of the anatomy with the location of the catheter superimposed. The anatomy can be viewed with a relatively low resolution since the cardiac chamber and the blood vessels are transparent to the x-ray radiation.

More recently, several technologies have been developed to ease the process of cardiac catheterization, mainly by enabling the physician to follow the path of the tip of the catheter inside the blood vessel. Some of this technology is based on digital subtraction radiography technology that enables viewing the blood vessel after the injection of a radio contrast dye and superimposing on that image the path of the catheter. These technologies necessitate the use of radiopaque dyes which are a major cause of morbidity in high-risk patients during cardiac catheterization.

U.S. Pat. No. 5,042,486 to Pfeiller et al., the disclosure of which is incorporated herein by reference, describes a method in which the position of a catheter tip is located using electromagnetic fields. The catheter is introduced and the tip location is followed. The path of the tip is superimposed on the pre-registered image of the blood vessel or the organ, through which the catheter was advanced. However, this technology requires acquisition and processing of images prior to the procedure and involves a highly sophisticated and time-consuming procedure for the correct alignment of the image acquired previous to this procedure, and the orientation and location of the blood vessel or the organ during the catheterization procedure itself.

U.S. Pat. No. 4,821,731 to Martinelli et al., the disclosure of which is incorporated herein by reference, discloses a method for internal imaging of a living body using ultrasound. In this patent the position of an ultrasound imaging catheter is determined by computing the relative position of the catheter using the response of an ultrasound transducer to a reference signal and by computing the angular orientation of the catheter about its axis by determining the signal induced in a single coil by substantially perpendicular magnetic fields of different frequencies. The ultrasound transducer is also used to send and detect ultrasound signals in a direction perpendicular to the catheter axis. By rotating the catheter and moving it along its axis an ultrasound image may be generated. The catheter is also described as being capable of transmitting a laser beam to the end thereof to ablate tissue from lesions on the walls of arteries.

A catheter which can be located in a patient using an ultrasound transmitter located in the catheter, is disclosed in U.S. Pat. No. 4,697,595 and in the technical note "Ultrasonically Marked Catheter, a Method for Positive Echographic Catheter Position and Identification", Bryer et al., Medical and Biological Engineering and Computing, May, 1985, pages 268–271. Also, U.S. Pat. No. 5,042,486 discloses a catheter which can be located in patients using non-ionizing fields and suitably imposing catheter location on a previously obtained radiological image of the blood vessel.

PCT Patent Publication WO 94/0938, the disclosure of which is incorporated herein by reference, describes a system using a single-coil type sensor which is coaxial with the long axis of a catheter and which senses fields which are generated by three multicoil generators external to the body of a patient.

Other methods and apparatus for the determination of the position of a catheter or endoscope are shown in U.S. Pat. Nos. 5,253,647; 5,057,095; 4,095,698; 5,318,025; 5,271,400; 5,211,165; 5,265,610; 5,255,680; 5,251,635 and 5,265,611.

U.S. Pat. No. 3,644,825 describes a system which uses the relative motion of a sensor in the determination of its position. The relative motion supplies information to the sensing coils needed to identify position and orientation. However, such a solution is not applicable to identifying position and location of the object where there is no relative motion between the object and the reference frame.

U.S. Pat. No. 3,868,565, the disclosure of which is incorporated herein by reference, comprises a tracking system for continuously determining the relative position and orientation of a remote object. This tracking system includes orthogonally positioned loops for both a plurality of sensors and a plurality of radiating antennas. With the proper excitation currents to those loops, the radiating antennas generate an electromagnetic field that is radiated from those antennas to the sensor. The tracking system operates as a closed loop system where a controlling means measures the field that is-received at the sensor at the remote object and feeds the information back to radiating antennas to provide a nutating field radiating as a pointing vector towards the remote object. Accordingly, the pointing vector gives the direction to the sensing antenna from the radiating antenna.

Similarly, Kuipers describes in his U.S. Pat. No. 4,017,858, the disclosure of which is incorporated herein by reference, an electromagnetic field which rotates about a pointing vector and is used both to track or locate the remote object in addition to determining the relative orientation of the object. This system, wherein the radiating coils are charged with the properly designed wave forms, generates a magnetic field which, in a closed loop manner, can be fed into processing means to generate the information needed to determine an orientation of a remote object.

U.S. Pat. No. 4,054,881, the disclosure of which is incorporated herein by reference, describes a non-tracking system for determining the position and location of a remote object with respect to a reference frame. This is accomplished by applying electrical signals to each of three mutually-orthogonal, radiating antennas, the electrical signals being multiplexed with respect to each other and containing information characterizing the polarity and magnetic moment of the radiated electromagnetic fields. The radiated fields are detected and measured by the three mutually orthogonal receiving antennas having a known relationship to the remote object, which produce nine parameters. These nine parameters, in combination with one known position or orientation parameter, are sufficient to determine the position and orientation parameters of the receiving antennas with respect to the position and orientation of the radiating antennas.

U.S. Pat. No. 4,849,692, the disclosure of which is incorporated herein by reference, describes a quantitative method for measuring the relative position and orientation of two bodies in the presence of metals. Measuring the position and orientation of receiving antennas with respect to the transmitting antennas is achieved using direct current electromagnetic field signals. Electromagnetic radiation is designed to be transmitted in a sequence by each of the mutually orthogonal radiating antennas. A receiving antenna measures the values of transmitted direct current magnetic fields, one dimension at a time, and those of the earth's magnetic field as well. This method requires repetitive acquisition and computations to determine position and location of remote objects.

Other methods which are known in the art for determining multi-dimensional positioning and orientation for aircraft and for helmets are described in U.S. Pat. No. 4,849,692, European patent publication 0 576 187 A1, GB patent publication 2 197 078 A and U.S. Pat. No. 4,314,251 the disclosures of which are incorporated herein by reference.

The above described prior art which is for use in non-medical applications, utilizes sensors and other structures which are not suitable for use in catheters. Those references which are described as being useful for medical probes generally give less than six dimensional information (three position coordinates and three angular coordinates).

In previous, as yet unpublished applications assigned to the assignee of the present application, U.S. patent application Ser. No. 08/094,539 now U.S. Pat. No. 5,391,199, filed Jul. 20, 1993 and PCT Application PCT/US94/08352 filed Jul. 20, 1994, the disclosures of which are incorporated herein by reference, a system is disclosed which incorporates a catheter which includes a position measuring device which can determine the position of the catheter in three dimensions, but not its orientation. In these applications, this catheter is used to map the electrical activity at the inner walls of the heart and to ablate portions of the heart muscle in response to such mappings. The position of the catheter used for the mapping/ablation function is determined with reference to three position detecting devices which are positioned against the inner wall of the heart at three different stable locations to form a reference plane.

SUMMARY OF THE INVENTION

In general the present application discloses a catheter locating means and method that offers quantitative, high resolution locating information that, when assimilated with sensed local information results in a high resolution, detailed map of the information. This map may optionally be superimposed on an image or other representation of the organ architecture.

The locating means preferably generates continuous location and orientation information concerning a remote object, in particular a catheter, relative to a reference frame, in a non-iterative manner.

One aspect of the present invention relates to the provision of a new six-dimensional positioning apparatus suitable for use with a catheter.

In a preferred embodiment of this system, a plurality of non-concentric coils are placed in a catheter adjacent a locatable site, for example, its distal end. The coils preferably have orthogonal axis. The relative positioning of the coils differs from that described in the prior art in that the coils are separated in space and are not concentric. These coils generate signals in response to externally applied magnetic fields which allows for the computation of six position and orientation dimensions.

A second aspect of the present invention is directed toward a new method for computing multi-dimensional position and orientation of a coil system from signals produced by the coils in response to a system of externally applied electromagnetic fields.

A third aspect of the present invention allows for the mapping of the interior of the heart in a manner similar to that described in the above-referenced patent applications assigned to the assignee of the present application, with the simplification that only a single six-dimensional location/orientation detection sensor is used for reference.

A fourth aspect of the present invention involves an ultrasonic or other imaging probe having a six-dimensional positioning capability in response to external electromagnetic fields. Use of such a probe obviates the use of ionizing radiation or sonic sensing for position determination and gives ultrasonic or other imaging information whose direction and orientation is completely known.

A fifth aspect of the invention involves methods and apparatus for adding a controlled change in orientation to a catheter, thereby to allow for maneuvering of the cathode and its easy placement.

A sixth aspect of the invention utilizes the controlled change in orientation to allow for two or three-dimensional imaging using a non-scanning probe, such as an ultrasound probe or for three-dimensional scanning using a two-dimensional scanning probe.

There is therefore provided, in accordance with a preferred embodiment of the invention, a locating system for determining the location and orientation of an invasive medical instrument, for example a catheter or endoscope, relative to a reference frame, comprising:

a plurality of field generators which generate known, distinguishable fields, preferably continuous AC magnetic fields, in response to drive signals;

a plurality of sensors situated in the invasive medical instrument proximate the distal end thereof which generate sensor signals in response to said fields; and a signal processor which has an input for a plurality of signals corresponding to said drive signals and said sensor signals and which produces the three location coordinates and three orientation coordinates of a point on the invasive medical instrument.

Preferably one or both of the plurality of field generators or sensors comprises three distinguishable, non-overlapping, generators or sensors.

In a preferred embodiment of the invention, each sensor comprises a coil. Preferably, said plurality of coils have axes which intersect within a coil. When said plurality of coils comprises three coils, said coils preferably have axes which do not all intersect in a point.

Preferably, the signal processor cross-correlates the signals corresponding to the drive and sensor signals.

Preferably, the fields generated by each of the generators have a different frequency, a different phase, or both a different frequency and a different phase.

In a preferred embodiment of the invention the field generated by each field generator has a different frequency, preferably frequencies which are each integer multiples of a given frequency. Preferably, the duration of the cross-correlation of the inputs is the minimal common product of the integer multipliers divided by the given frequency.

Preferably, the results of the cross-correlation are used to calculate the contribution of each field generator to the signal generated by each said sensor.

In a preferred embodiment of the invention the locating system includes a display system for displaying the position of the point on the invasive medical instrument.

Preferably, the locating system further comprises a reference instrument which includes a plurality of non-overlapping sensors situated in the reference instrument which sensors generate sensor signals in response to said fields, wherein said display system displays the position of the point on the invasive medical instrument relative to the position of a point on the reference instrument. Preferably the reference instrument is an invasive medical instrument. Preferably, the sensors are situated proximate the distal end of the reference invasive medical instrument.

In a preferred embodiment of the invention the locating system includes an additional sensor on a portion of the invasive medical instrument which senses a local condition.

Preferably, the additional sensor senses local electrical signals, for example electrical signals from the endocardium of the patient's heart, and transfers them to terminals external to the patient's body.

In a preferred embodiment of the invention the signal processor processes the position and orientation coordinate signals and the local electrical signals acquired at a plurality of points on the endocardium to generate a map that represents the propagation of electrical signals through tissue in the patient's body.

In a preferred embodiment of the invention the additional sensor supplies electrical energy to the endocardium for ablating a portion of the endocardium.

Preferably the locating system includes an electrode adapted for supplying electrical energy to the endocardium for ablating a portion of the endocardium.

In a preferred embodiment of the invention the additional sensor is an ultrasonic transmitter/receiver.

Preferably, the ultrasonic transmitter/receiver provides a less than three dimensional representation of the acoustic properties of tissue beyond the distal end.

In a preferred embodiment of the invention, the distal end is deflectable. Preferably, the system includes image reconstruction circuitry which receives a plurality of said less than three dimensional representations acquired at different orientations of the distal end and produces a three dimensional map of the acoustic properties of tissue at least partially surrounding the distal end.

There is further provided, in accordance with a preferred embodiment of the invention, an imaging system for intra-body ultrasonic imaging comprising:

a invasive medical instrument, preferably, a catheter or endoscope, having an axial-looking ultrasonic imaging transducer at the distal end thereof which generated a representation, preferably a one or two dimensional representation, of the acoustic properties of tissue beyond the distal end;

means for manipulating the distal end to change the orientation thereof; and image reconstruction circuitry which receives a plurality of said representations acquired at different orientations of the distal end and produces a three dimensional map of the acoustic properties of tissue at least partially surrounding the distal end from said plurality of representations.

Preferably, the imaging system further comprises:

a plurality of field generators which generate known, distinguishable fields in response to drive signals;

a plurality of sensors situated in the invasive medical instrument proximate the distal end thereof which generate sensor signals in response to said fields; and a signal processor which has an input for a plurality of signals corresponding to said drive signals and said sensor signals and which produces three location coordinates and three orientation coordinates of the a point on the transducer.

There is further provided a method of determining the position and orientation of an invasive medical instrument, for example a catheter or endoscope, having a distal end, comprising:

(a) generating a plurality, preferably three, of distinguishable, geometrically different AC magnetic fields;

(b) sensing the AC magnetic fields at the sensors at a plurality of points proximate the distal end; and (c) computing six dimensions of position and orientation of a portion of the invasive medical instrument responsive to signals representative of the generated magnetic fields and the sensed magnetic fields.

Preferably, the AC magnetic field is sensed at three points of the invasive medical instrument.

There is further provided, in accordance with a preferred embodiment of the invention, an ultrasonic intra-body imaging method comprising:

(a) inserting an ultrasonic transducer into the body, said ultrasonic transducer producing a representation of the acoustic properties of tissue beyond an end of the transducer;

(b) manipulating the orientation of the transducer to provide a plurality of said representations; and (c) constructing a three dimensional map of the acoustic properties of the tissue in a region at least partially surrounding the end of the transducer from said plurality of representations.

Preferably, the method includes determining the six dimensions of position and orientation of the transducer for each of the representations.

Preferably, the representation is a less than three dimensional representation.

There is further provided an invasive medical instrument, for example a catheter or endoscope, comprising a plurality of magnetic field sensors, preferably coils, proximate the distal end thereof.

Preferably the plurality of coils have axes which intersect within a coil. Where the plurality is three, the said coils have axes which do not all intersect in a point.

In a preferred embodiment of the invention, the instrument comprises an ultrasound transducer at said distal end. Preferably, the ultrasound transducer provides a representation, preferably a one or two dimensional representation, of the acoustic properties of tissue beyond and along the axis of the catheter.

In a preferred embodiment of the invention, the instrument further comprises an electrical probe at said distal end. The probe is preferably adapted to sense electrical signals generated by tissue which is in contact and conduct said signals to the proximal end of the catheter and/or to supply an ablative electrical signal to tissue contacting said terminal. In a preferred embodiment of the invention, the instrument includes a sensor for measuring local chemistry at the distal end.

Preferably, the instrument includes means for changing the orientation of the distal end.

There is further provided, in accordance with a preferred embodiment of the invention, apparatus for steering the distal end of an invasive medical instrument, such as a catheter or endoscope, comprising:

a relatively more flexible wire passing through the catheter that is attached to the distal end and has a bend near the distal end;

a relatively more rigid sleeve which is straight near the distal end and which slideably holds the wire thereat, whereby when the sleeve is slid over the wire, the wire and distal end are straightened.

Preferably, the instrument has a lengthwise axis and the wire is sited off the axis of the instrument.

There is further provided apparatus for steering the distal end of an invasive medical instrument comprising:

a flat relatively flexible portion being slit along a portion of the length thereof to form two portions which are attached at a first end thereof, said first end being attached to the distal end of the instrument;

a pair of wires, one end of each of which being attached to one of said portions at a second end thereof; and means for changing the relative lengths of the wires whereby the flexible element is bent, thereby steering the distal end of the instrument.

There is further provided, in accordance with a preferred embodiment of the invention, a method of producing a three dimensional image of the internal surface of an internal body organ comprising:

measuring the distance to said surface at a plurality of orientations from within the internal surface; and assembling the distances to form an image of the surface.

Preferably, the measurement of distances is made from a plurality of points within the organ. Preferably, the measurement of distances is preformed utilizing an ultrasonic transducer.

DETAILED DESCRIPTION OF THE PREFERRED EMBODIMENTS

Figure 1:
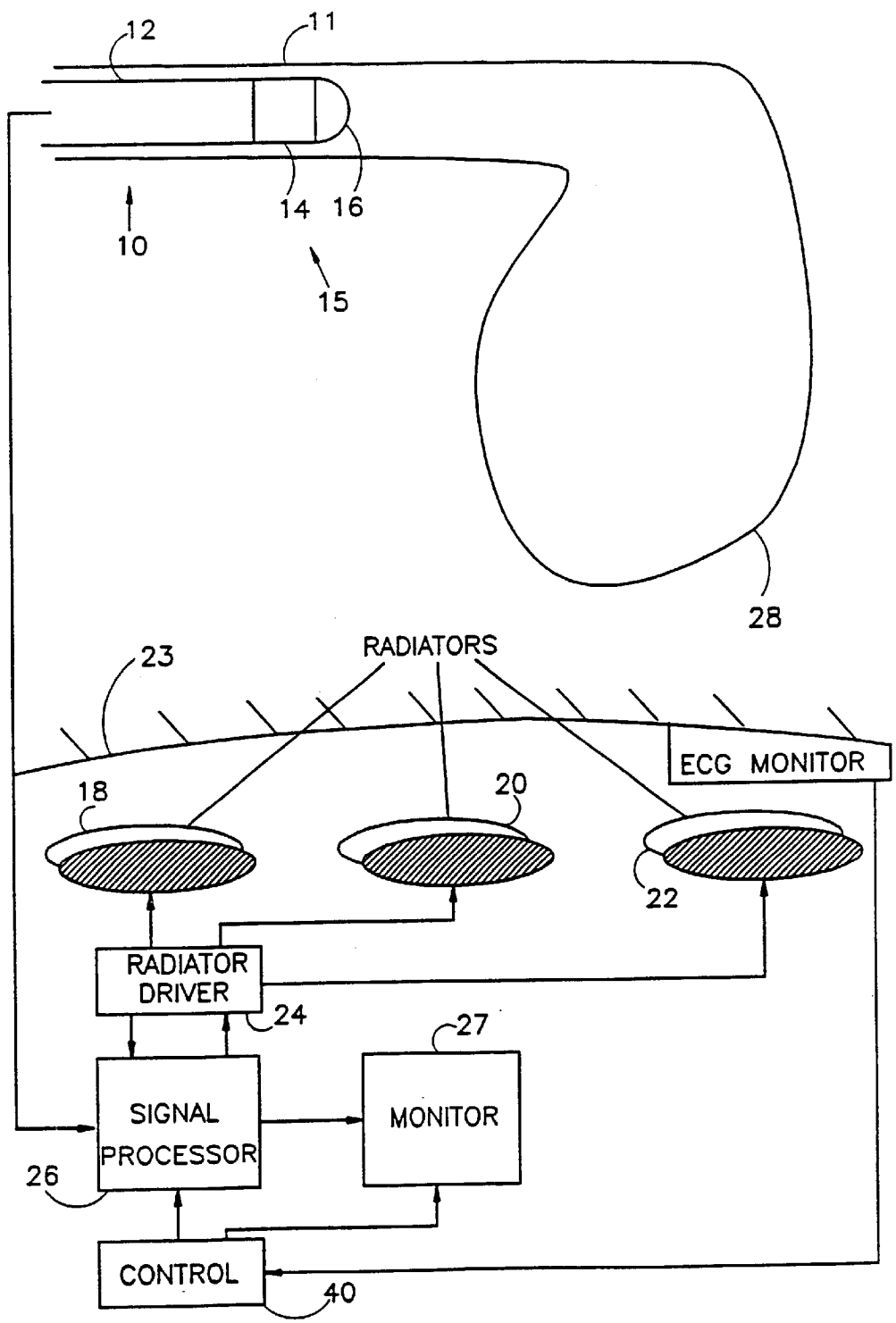
FIG. 1 is a pictorial representation of the application of a system for six-dimensional position and bearing determination, in accordance with a preferred embodiment of the invention to a catheter located in a human body.

FIG. 1 shows a pictorial representation of a basic preferred application of the invention to the human body. In this application, a catheter 10 is inserted into an artery 11 of a patient using standard techniques. Catheter 10 comprises a body 12, a locating sensor 14 and an active portion 16 at the distal end 15 of the catheter. The active portion 16, in accordance with various preferred embodiments of the invention, may include an electrical sensor, an ultrasound head, a fiber optic viewing head, an electrical stimulator, an electrical or laser ablator, an ionic sensor, an oxygen or carbon dioxide sensor, an accelerometer, a blood pressure or temperature sensor or a cryogenic probe. In general the catheter will include leads, light guides, wave guides, etc. for energizing the active portion in response to commands of an operator.

The position and orientation of the distal end of the catheter is ascertained by determining the position of the locating sensor. In a preferred embodiment of the invention, the locating sensor comprises two or three antennas, for example coils which are irradiated by two or three radiators 18, 20 and 22, which are outside the body surface 23 of the patient.

It should be understood that placement of the radiators, as well as their size and shape, will vary according to the application of the invention. Preferably the radiators useful in a medical application comprise wound annular coils from about 2 to 20 cm in diameter (O.D.) and from about 0.5 to 2 cm thick, in a coplanar, triangular arrangement where the centers of the coils are from about 2 to 30 cm apart. Bar-shaped radiators or even triangular or square-shaped coils could also be useful for such medical applications. Moreover, in instances where a prone patient will be the subject of a procedure involving the instant technology, the radiators are preferably positioned in or below the surface upon which the patient is resting, substantially directly below the portion of the patient's body where a procedure is being performed. In other applications, the radiators may be fairly close to the skin of the patient.

The three radiators are driven by a radiator driver 24, preferably in a manner described below, and the signals received by the receiving antennas are amplified and processed, together with a representation of the signals used to drive radiators 18, 20 and 22, preferably in the manner described below, in a signal processor 26 to provide a display or other indication of the position and orientation of the distal end 15 on a monitor 27.

Radiators 18, 20 and 22 may be arranged in any convenient position and orientation, so long as they are fixed in respect to some reference frame, and so long as the radiators are non-overlapping, that is, there are no two radiators with the exact, identical location and orientation. When driven by radiator driver 24, the radiators generate a multiplicity of distinguishable AC magnetic fields that form the magnetic field sensed by receiving antennas in the locating sensor.

The magnetic fields are distinguishable with regard to the frequency, phase, or both frequency and phase of the signals in the respective magnetic fields. Time multiplexing is also possible.

In practice the active end of the catheter may be used to gather information, such as ultrasound echo information, electrical activity information etc., and optionally to perform certain procedures on the arteries (or veins) or within an organ chamber 28 to which the artery (or vein) leads. Particular examples of organ chambers are the chambers of the heart, brain or gastrointestinal tract. It is a particular object of some aspects of the present invention to more accurately map the electrical activity of the heart and to more accurately image the walls of the heart, as will be described in more detail below.

Figure 2:
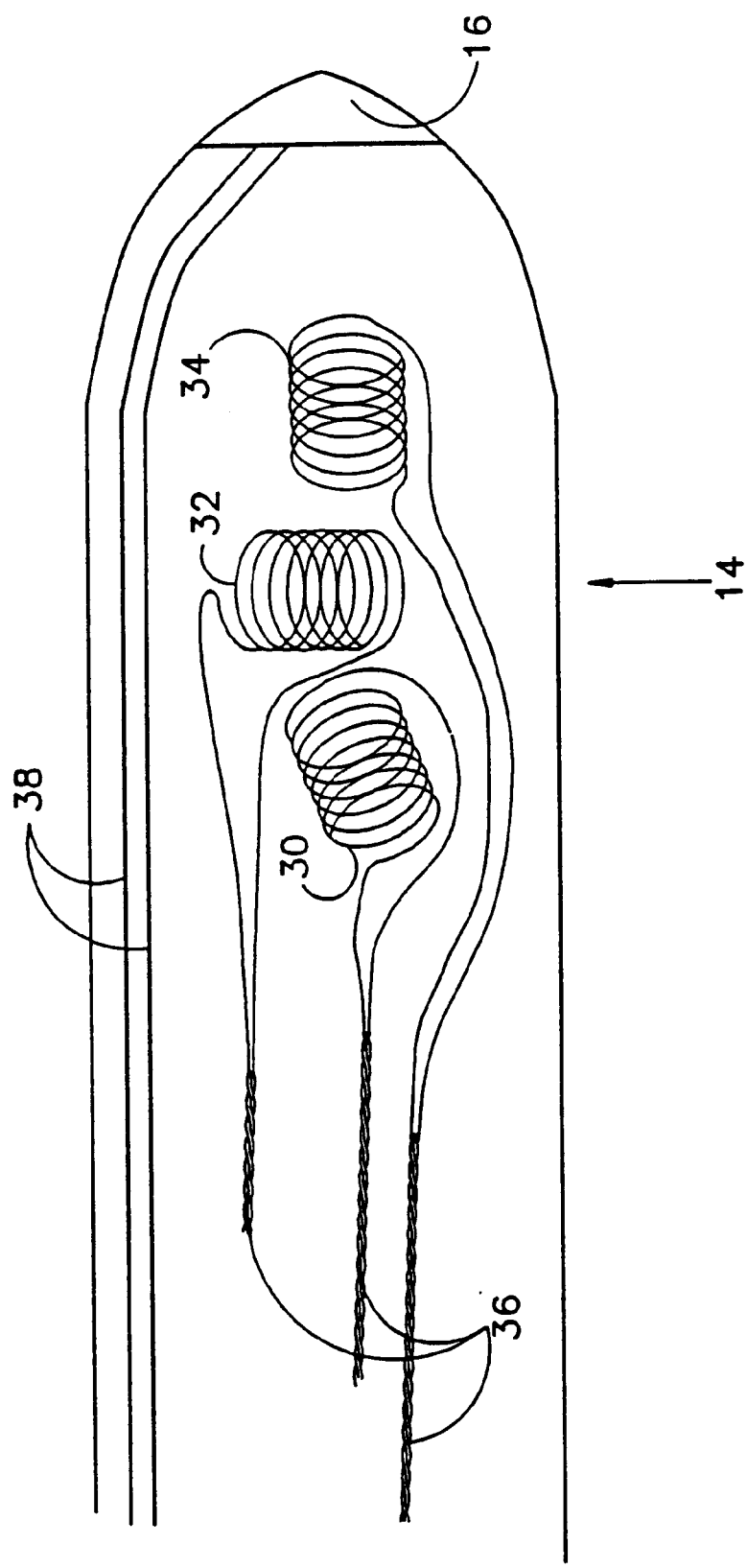
FIG. 2 is a schematic, cut-away illustration of a generalized catheter having a six-dimensional location capability in accordance with a preferred embodiment of the present invention.
Figure 3:
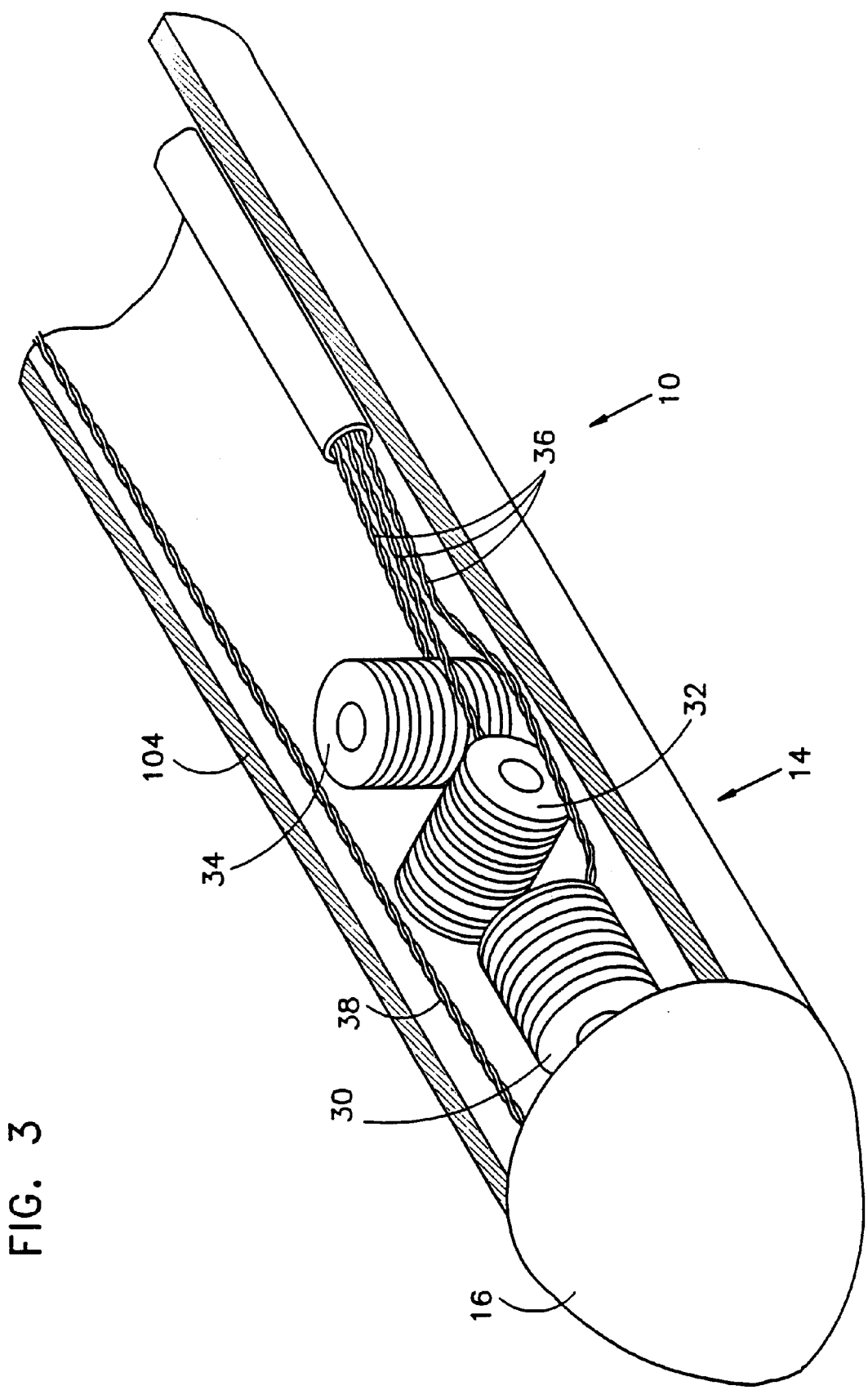
FIG. 3 is a more graphic illustration of a portion of the probe showing a preferred embodiment of a sensor for six-dimensional location.

FIG. 2 shows a schematic illustration of a preferred embodiment of the distal end of catheter 10. A graphic illustration of locating sensor 14 is shown in FIG. 3. Sensor 14 preferably includes two or more and more preferably three sensor coils 30, 32 and 34 wound on air cores. In a preferred embodiment of the invention the coils have mutually orthogonal axes, one of which is conveniently aligned with the long axis of the catheter. Unlike prior art location sensors (used for other applications) which contain three coils that are concentrically located, or at least whose axes intercept, the coils of the preferred embodiment of the invention are closely spaced along the axis of the catheter to reduce the diameter of the locating sensor and thus make the sensor suitable for incorporation into a catheter.

For most aspects of the present invention, quantitative measurement of the position and orientation of the catheter distal end relative to a reference frame is necessary. This requires at least two non-overlapping radiators that generate at least two distinguishable AC magnetic fields, the radiators' respective positions and orientations relative to the reference frame being known; a radiator driver which preferably continuously supplies the radiators with AC signals to generate the AC magnetic fields; and a location sensor, consisting of at least two non-parallel sensors to measure the magnetic field flux resulting from the at least two distinguishable magnetic fields. The number of radiators times the number of sensors is equal to or greater than the number of degrees of freedom of the desired quantitative measurement of the position and orientation of the sensors relative to the reference frame.

Since, in a preferred embodiment of the invention it is preferred to determine the six position and orientation coordinates of the distal tip of the catheter, at least two coils are required in location sensor 14. Preferably three coils are used to improve the accuracy and reliability of the position measurement. In some applications where fewer dimensions are required, only a single coil may be necessary in locating sensor 14.

Leads 36 are used to carry signals detected by the sensor coils to signal processor, via the proximal end of the catheter, for processing to generate the required position information. Preferably, leads 36 are twisted pairs to reduce pick-up and may be further electrically shielded.

In a preferred embodiment of the invention, coils 30, 32 and 34 have an inner diameter of 0.5 mm and have 800 turns of 16 micrometer diameter to give an overall coil diameter of 1–1.2 mm. The effective capture area of the coil is preferably about 400 mm$^2$. It will be understood that these dimensions may vary over a considerable range and are only representative of a preferred range of dimensions. In particular, the size of the coils could be as small as 0.3 mm (with some loss of sensitivity) and as large as 2 or more mm. The wire size can range from 10–31 micrometers and the number of turns between 300 and 2600, depending on the maximum allowable size and the wire diameter. The effective capture area should be made as large as feasible, consistent with the overall size requirements. While the preferred sensor coil shape is cylindrical, other shapes can also be used. For example a barrel shaped coil can have more turns than a cylindrical shaped coil for the same diameter of catheter. Also, square or other shaped coils may be useful depending on the geometry of the catheter.

Leads 38 are used to power active portion 16 and/or to receive signals therefrom. The nature of leads 38, which may vary and may, for example, include an optical waveguide or other transmission media as appropriate to their task.

For example, an electrode located on the distal tip of the catheter records local cardiac electrical activity, for example, on the endocardium. These local electrograms (ECG's) are transferred via leads 38 to the proximal end of the catheter and fed into an ECG amplifier. The amplified ECG signals are transferred to the control system that presents to the physician the local electrogram morphology acquired from the site whose location was determined at the same time.

Figure 4:
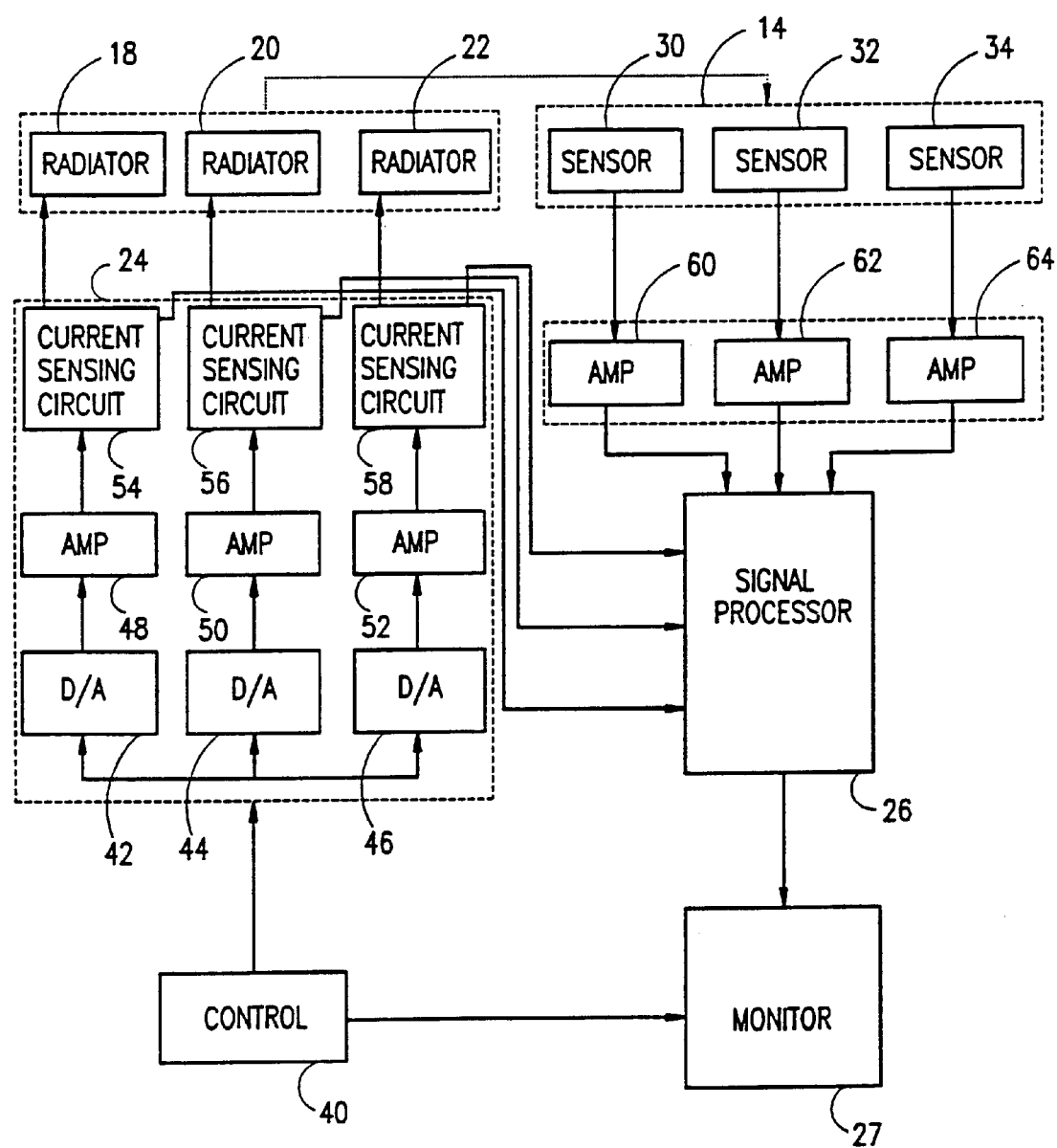
FIG. 4 is a block diagram of circuitry used to determine the six-dimensional coordinates of a catheter, in accordance with a preferred embodiment of the invention.

FIG. 4 is a block diagram of preferred circuitry used in computing the position of locating sensor 14. In this exemplary embodiment, three radiators 18, 20 and 22 and three sensor coils 30, 32 and 34 are used. Radiator driver 24 provides distinguishable, simultaneous AC current signals to each radiator. Control circuitry 40 utilizes D/A convertors 42, 44 and 46 to generate three sine waves of three different frequencies, $f_1$, $f_2$ and $f_3$, which are output separately to signal amplifiers 48, 50 and 52.

In order to achieve a fast response locating system the use of slow responding filters has been eliminated by using cross-correlation of the radiated and the received signals. This cross-correlation is performed over a window in time which contains an integer number of the cycle lengths of the three radiated signals. Use of an integer number of cycles generally results in a decrease in processing errors and a more accurate determination of the relative amplitude and phase of the signals received by the sensor coils. If non-integral cycle lengths are used an error in the cross-correlation generally results, unless a very long correlation window is used.

If a short correlation window is used, (the shortest is the minimal common product of the cycle times), the ratio between frequencies should be a rational number. The frequency of a radiator c, $f_c$, where c=1, 2 or 3 should satisfy the equation:

$$f_c = n_c \cdot f_b \qquad (1)$$

where $n_c$ is any positive integer such that n1≠n2, n2≠n3, and n3≠n1, and $f_b$ is an arbitrary base frequency to assure that integral cycle lengths can be used for cross-correlation.

The radiating driver amplifier output signals are delivered to the radiators through current sensitive circuitry 54, 56 and 58, such as a resistor, loop or more sophisticated circuitry as is known in the art. The current-sensitive circuitry produces an output which represents the amplitude and phase of the driving signal for the radiators and which is passed to signal processor 26. With this arrangement, the three radiators will generate a magnetic field composed of three differently oriented field components each having a different known frequency. Each of these field components will be sensed by each of sensor coils 30, 32 and 34 which will each produce a signal composed of three frequency components having different amplitudes and phases depending on the relative distance and orientation of the particular sensor coil and particular radiator which radiates a particular frequency.

The outputs signals of sensors 30, 32 and 34 are amplified in amplifiers 60, 62 and 64 respectively and passed on to signal processor 26.

Figure 5:
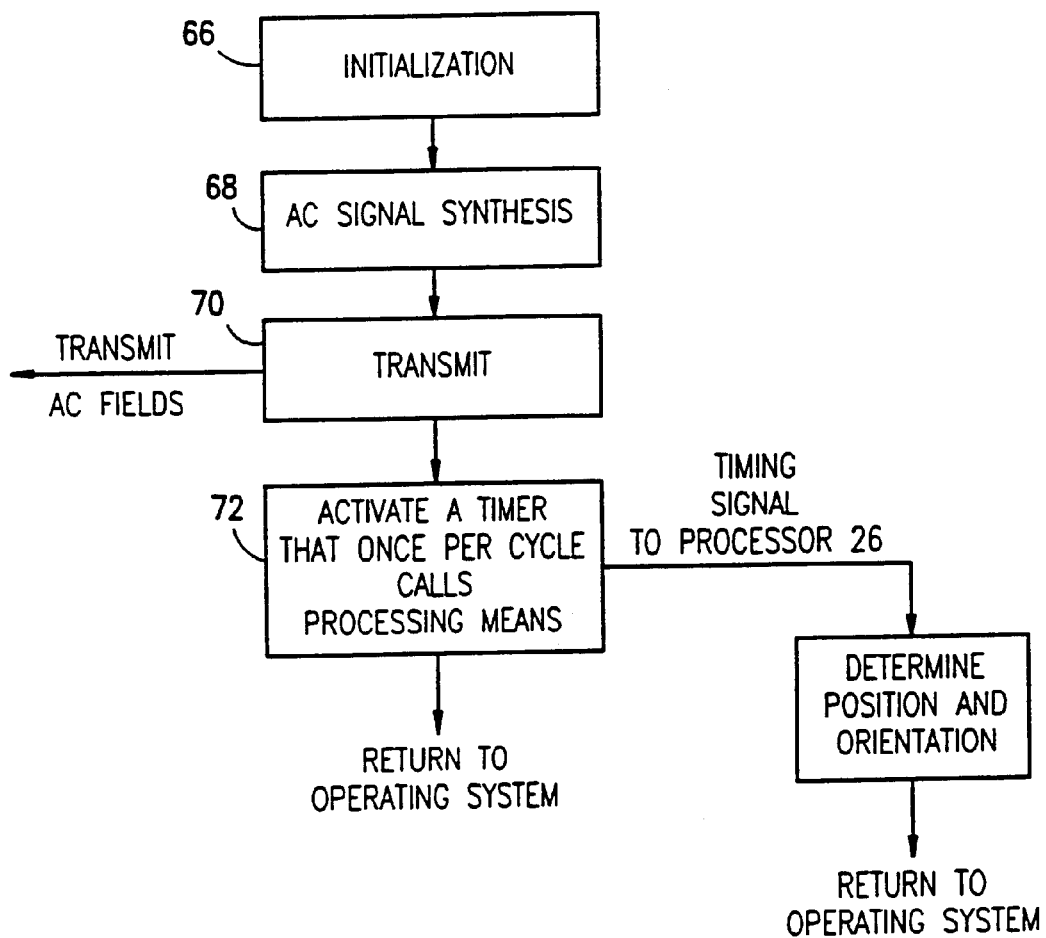
FIG. 5 shows in expanded detail the basic flow chart representing a control sequence and its application to the block diagram of FIG. 4, in accordance with a preferred embodiment of the invention.

FIG. 5 shows in expanded detail the basic flow chart representing a control sequence and its application to the circuitry of FIG. 4. During the initialization phase, indicated by block 66, the frequencies of the three sine waves, the physical position and orientation of radiators 18, 20 and 22 in respect to a reference frame, the properties of the radiators and sensors and the coordinates of a single point in the mapping field are defined. Sine waves having respective frequencies $f_1$, $f_2$ and $f_3$ are synthesized as indicated by block 68, for example in control 40. These generated frequencies are transmitted, preferably continuously, by radiators 18, 20 and 22 as indicated by block 70 and as described above with reference to FIG. 4. The control sequence enters a timing loop 72 that periodically sends signals to activate the signal processor to cross-correlate the coil sensor signals with the radiated signals and to calculate the orientation and position of locating sensor 14 relative to the reference frame.

Both analog and digital embodiments of signal processing are possible in accordance with preferred embodiments of the invention. These different approaches can be modified in a variety of ways by those skilled in the art, and can be combined in different modes in order to practice them simultaneously. Some applications of the present invention would benefit from the digital approach, while the analog approach may be the preferable solution in other cases.

Figure 6:
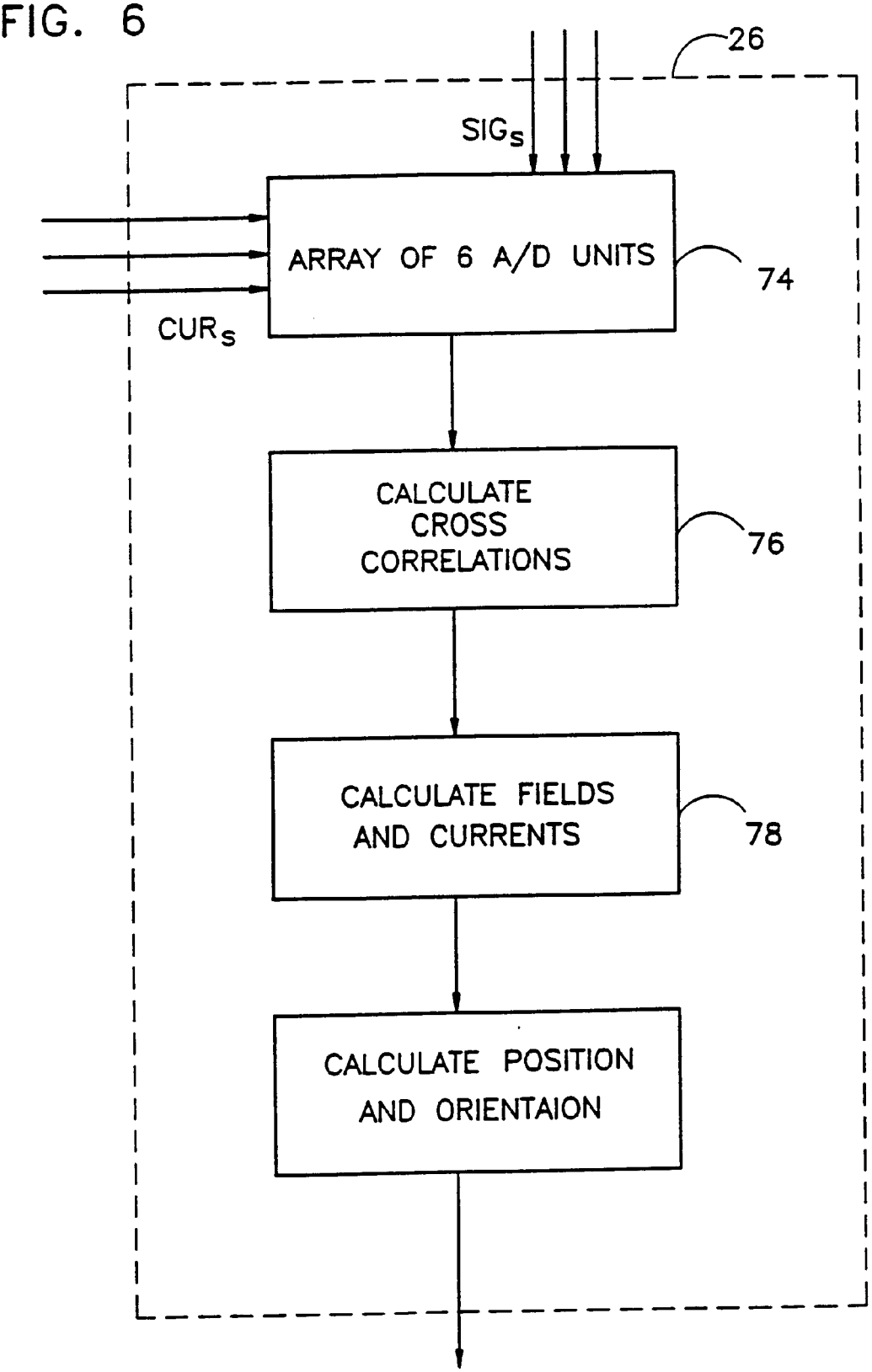
FIG. 6 is a block diagram representing digital signal processing in the signal processor in accordance with a preferred embodiment of the invention.

The digital embodiment is described in conjunction with FIG. 6, which is a functional block diagram of signal processor 26. The inputs to the processing block are the signals from amplifiers 60, 62 and 64 (the sensor coil signals) denoted by SIG and inputs from current sensing circuits 52, 56 and 58 denoted as CUR. In this embodiment the six input signals are converted from analog to digital signals by an array of A/D converters 74. The sampled digital signals are passed to the "calculate cross correlation" block 76, which may consist of dedicated circuitry or which may be performed by a dedicated or shared microprocessor. Using the six data streams (three AC currents flowing through the radiators and three sensor readings) the cross correlation elements can be calculated using the following method:

Given that
  $SIG_s$ is the amplified output of sensor s, where s=1, 2 or 3;
  $CUR_c$ is the current flowing through radiator c, where c=1, 2 or 3;
  $f_b$ is an arbitrary base frequency;
  $f_0$ is the sampling frequency which is an integral multiple of $f_b$; and
  and N is the correlation length in number of samples, $N = K(f_0/f_b)$, where K is any positive integer,
the correlation between CURc and the sine wave of frequency $f_c$ is:

$$A_c^I = (2/N) \cdot \sum CUR_c[i] \cdot \sin(2\pi f_c(i/f_0)); \qquad (3)$$

and the correlation between CURc and the cosine wave of frequency $f_c$ is:

$$A_c^Q = (2/N) \cdot \sum CUR_c[i] \cdot \cos(2\pi f_c(i/f_0)); \qquad (2)$$

where both summations are taken over i from 1 to N. The correlation between $SIG_s$ and the sine wave of frequency $f_c$ is $$B_{s,c}^I = (2/N) \cdot \sum SIG_s[i] \cdot \sin(2\pi f_s(i/f_0)); \qquad (4)$$

and the correlation between $SIG_s$ and the cosine wave of frequency $f_c$ is $$B_{s,c}^Q = (2/N) \cdot \sum SIG_s[i] \cdot \cos(2\pi f_c(i/f_0)); \qquad (5)$$

where both summations are taken over 1 from 1 to N.

A preferred ratio of $f_1$, $f_2$ and $F_3$ is 1, 2, 3 and preferred frequencies are 1, 2 and 3 kHz. The useful frequency range is believed to lie between 50 Hz and 50 kHz.

The calculation of the fields and currents, designated by block 78, can also be performed using either dedicated circuitry or a dedicated or shared microprocessor. The amplitude of the current through each radiator $A_c$ can be calculated using:

$$A_c = |A_c^I + jA_c^Q| \qquad (6)$$

and the magnitude of the field generated by each radiator, $|B_{s,c}|$, can be calculated using:

$$|B_{s,c}| = |B_{s,c}^I + jB_{s,c}^Q| \qquad (7)$$

The phase between the current in radiator c and the field sensed by sensor s, $\Psi_{s,c}$, is $$\phi_{s,c} = \arg(B_{s,c}^I + jB_{s,c}^Q) - \arg(A_c^I + jA_c^Q) - \Psi_s^0 \quad (8)$$

where $$\Psi_s^0$$

is the phase delay between the radiated field and the field as read by sensors s. The amplitude of the field generated by radiator c as sensed by sensor s is:

$$B_{s,c}=|B_{s,c}|, \text{ if } |\phi_{s,c}|<90° \quad (9A)$$

$$B_{s,c}=-|B_{s,c}|, \text{ if } |\phi_{s,c}|\geq 90° \quad (9b)$$

The magnetic field for every possible location and orientation of the sensor in the mappable space can be obtained by using:

1) The field equations of the radiators used in a specific embodiment,
2) The exact position and orientation of the radiators, and
3) The current flowing through the radiators $A_c$.

Preferably the contributions of each field generator are used to solve a set of field equations, which are dependent upon the field form. Solving these equation sets produces the location and orientation of the remote sensors, most preferably simultaneously.

More particularly, the field equations are derived specifically for each embodiment and are dependent on the geometry and characteristics of the radiators. In the preferred embodiment of the invention where the radiators are coils, the field equations can be described as follows:

For a coil with N turns a radius R and a current I, the radial field component at a distance r is $$B_r(I, \vec{r}, \cos\theta) = (2\pi R^2 10^{-7} \cdot NI/r^3) \cdot$$

$$\Sigma(2i+1)P_{2i}(0)\cdot(R/r)^{2i}\cdot P_{2i+1}(\cos\theta) \quad (10)$$

and the tangential field component is:

$$B_\theta(I, \vec{r}, \cos\theta) = (2\pi R^2 10^{-7} \cdot NI/r^3) \sum P_{2i+2}(0)(R/r)^{2i} P_{2i+1}^1 \cos\theta$$

where the sums are from i=0 to i=∞ and where $P_n(x)$ is a Legendre Polynomial of degree n, and calculated recursively by:

$$P_0(x)=1$$

$$P_1(x)=x$$

$$P_n(x)=1/n[(2n-1)\times P_{n-1}(x)-(n-1)P_{n-2}(x)] \quad (12)$$

$$P_n^1(x)$$

is a generalized Legendre Polynomial of degree n, and calculated by:

$$P_n^1(x) = -(n+1)\cdot x\cdot(P_n(x) - P_{n-1}(x))/(1-x^2)^{1/2} \text{ for } |X|<1 \quad (13)$$

$$= 0 \text{ for } |X|=1$$

Figure 7:
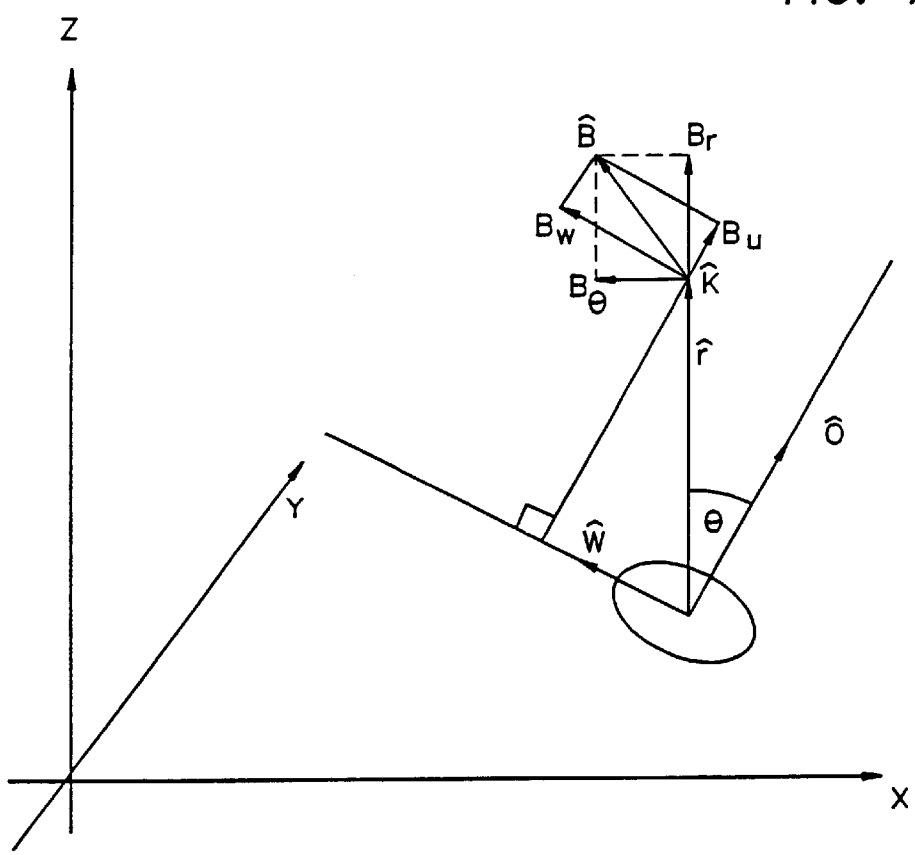
FIG. 7 is a three-dimensional graphic representation of the vectors forming the magnetic field at a point.

These field equations are correct for r>R for a radiator located in location $\vec{P}$. The field induced at location $\vec{K}$ is, as shown in FIG. 7, given by:

$$B=B_u \hat{O}+B_w \hat{W}$$

$$B_w=B_r \sin\theta+B_\theta \cos\theta$$

$$B_u=B_r \cos\theta-B_\theta \sin\theta \quad (14)$$

where $\hat{O}$ is a unit vector in the radial direction of the radiator located at $\vec{P}$ and $\hat{W}$ is a unit vector in the tangential direction of the radiator located at $\vec{P}$. Using this general field equation one can calculate the field at point $\vec{K}$ generated by each of the radiators.

The remote sensor orientation, denoted by $\hat{V}$ determines the field sensed by this sensor at this location ($\vec{K}$).

$$\vec{B}\cdot\hat{V}=B_{\hat{V}} \quad (15)$$

Therefore the field sensed by a remote sensor is $$B_{\hat{V}}=B(\vec{P}, \hat{O}, I, \vec{K}, \hat{V}) \quad (16)$$

where $\vec{K}$ and $\hat{V}$ are the unknown variables, and $\hat{O}$, $\vec{P}$ and I are the known variables for any given coil.

In the example embodiment there are three radiators; therefore there will be three known values of $\vec{P}$ and three known values of $\hat{O}$. The three sensors have a fixed and known location and orientation in the remote object reference frame. For each position and orientation of the remote object, one can compute the location and orientation of each sensor in the radiator reference frame and therefore compute the field sensed, $B_v$, for each radiator and each sensor. In the case of the present location system, each field sensed by each sensor from every radiator is measured and the field equations are solved to obtain the location and orientation of the remote object (x, y, z, $\epsilon,\xi$, and $\zeta$).

The results of this approach for the three radiator, three sensor system used here as an example, are nine non-linear algebraic equations with six variables (namely, x, y, z of the sensing means position and $\epsilon,\xi$, and $\zeta$ for the location sensor orientation) in the form of:

$$\{[F_{s,c}(x, y, z, \epsilon,\xi,\zeta)=B_{sc}]_{s=1,2,3}\}_{c=1,2,3} \quad (17)$$

In this embodiment of the invention, the nine sensor readings ($B_{s,c}$) are the measured quantity, and by solving this overdetermined system of equations (using a variety of known numerical methods such as the Newton-Raphson method for non-linear systems of equations or Multidimensional Secant Methods, specifically Broyden's method), the location and orientation of location sensor 14 is determined. A description of several possible numerical methods for solving such a set of equations is found in William H. Press et al, "Numerical Recipes in C. The Art of Scientific Computing", second edition, Cambridge University Press, 1992. The location sensor position and orientation are displayed on monitor 27.

An ECG monitor may be used to synchronize the acquisition of the signals from the sensor coils so as to remove cardiac motion artifacts from the position information. Furthermore, a reference sensor may be attached to a portion of an organ being tested or treated, such as the heart, which will be used to correct for breathing motion or patient movement. In this way, the acquired sensor positions may be referenced to the organ structure and not to an absolute outside reference frame, which is less significant.

In an analog based embodiment of signal processor 26, some of the parameters are calculated using analog circuitry.

Figure 8:
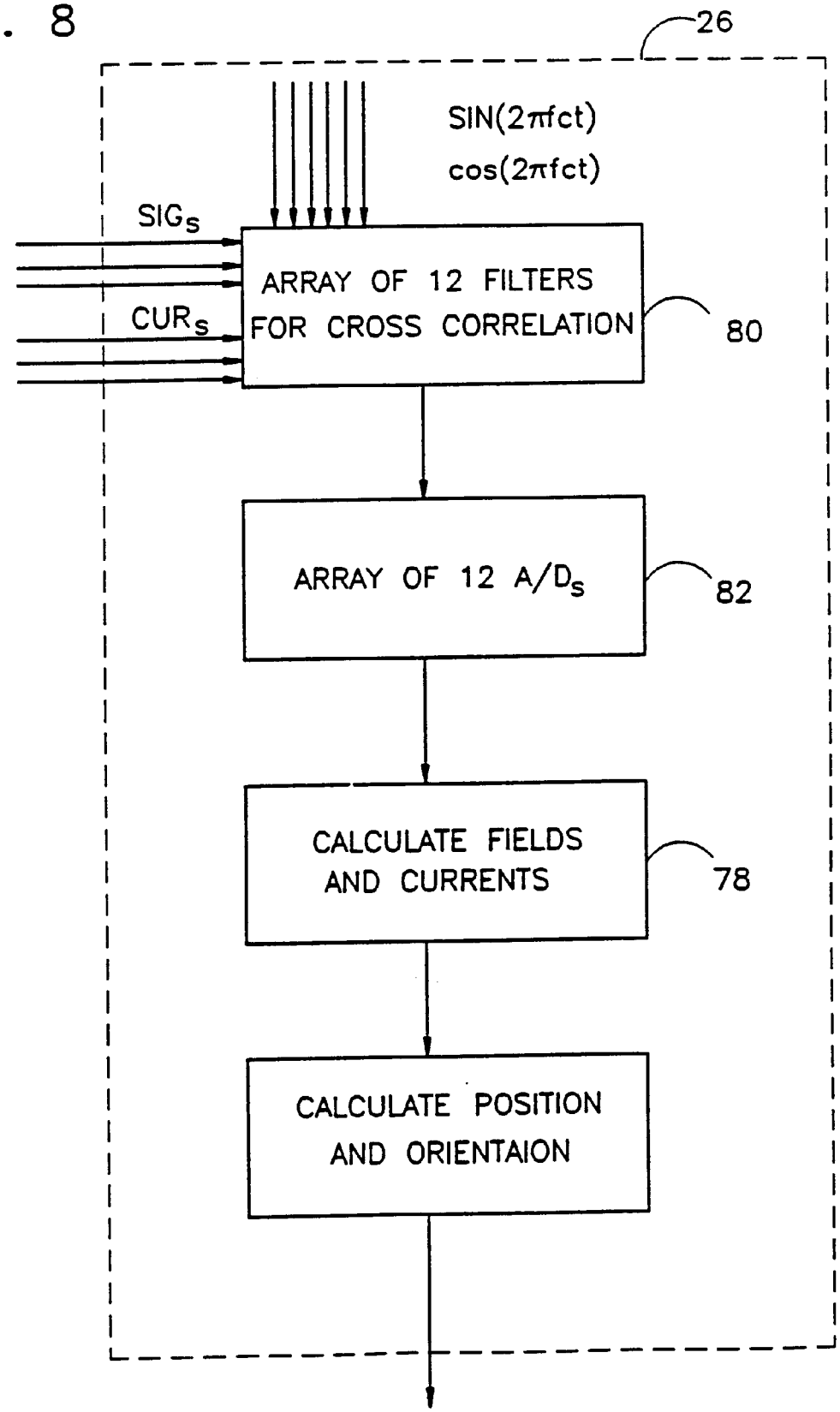
FIG. 8 is a block diagram representing analog signal processing in the signal processor, in accordance with a preferred embodiment of the invention.

FIG. 8 is a schematic of one analog based embodiment of signal processor 26. In this embodiment, three sine and three cosine wave signals of frequency $f_1$, $f_2$, and $f_3$, are used in addition to the SIG and CUR signals used in the embodiment of FIG. 6. The SIG and CUR signals are filtered by 12 phase sensitive filters (correlators) 80, such as are shown in FIG. 9 to produce signals indicative of the sine and cosine components of the SIG and CUR signals.

These analog signals are then passed to a set of A/D converters 82. The fields and currents and positions are calculated in the same manner as described above with respect to FIG. 6.

Figure 9:
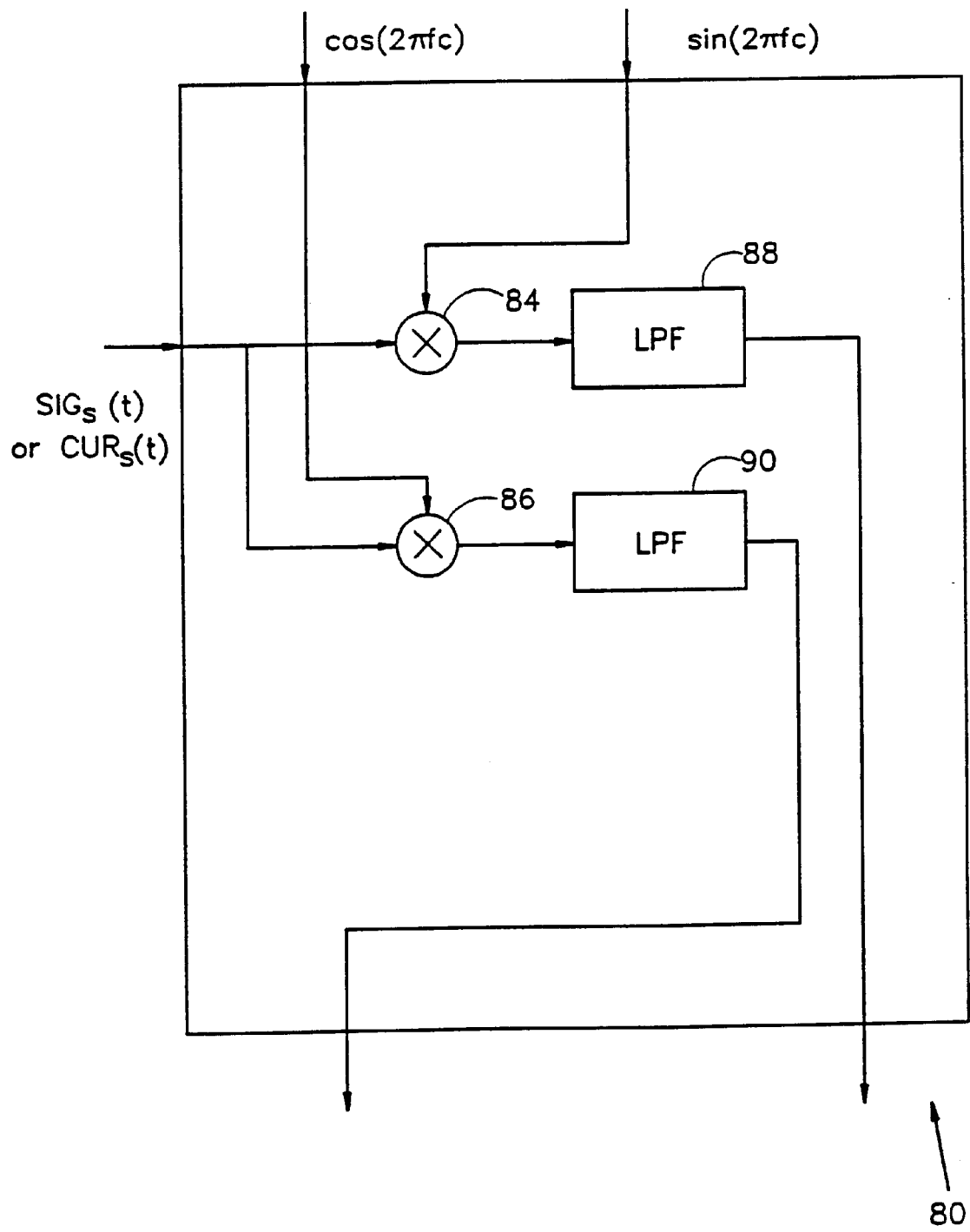
FIG. 9 is a simplified schematic of an analog filter element shown in FIG. 8, in accordance with a preferred embodiment of the invention.

FIG. 9 shows the expanded view of one possible embodiment of one of the analog filter elements of FIG. 8. Each analog filter unit has three inputs; a cosine wave $\cos(2\pi f_c)$, a sine wave $\sin(2\pi f_c)$, and the signal, either one of $SIG_s$ or $CUR_s$ from which the frequency component $f_c$ is to be extracted. Within the analog filter unit the signal is multiplied by $\sin(2\pi f_c)$ and $\cos(2\pi f_c)$ in multipliers 84 and 86. The results are passed through low pass filters 88 and 90 to obtain the desired components of the signal.

The description above primarily concerns acquiring information by a set of two or more sensors that is used to determine the position and orientation of a remote object or a point on a remote object such as a medical device or instrument. It is also within the scope of the invention that a remote object will have more than one set of sensors, preferably from 2 to 6 sets of sensors, that will provide sufficient parameters to determine the shape and/or configuration of a remote object, preferably relative to a reference frame. For example, if the catheter has additional sets of sensors located proximal to its distal tip, it would be possible to determine the shape and/or configuration of portions of the catheter. Similarly, for another invasive procedure such as a sigmoidoscopy or colonoscopy, it may be possible to determine the shape and/or configuration of some or all of the scope used.

The equipment necessary to practice the invention is mostly conventional. In one embodiment of the invention, the controller is a simple off-the-shelf 486 IBM compatible computer. The A/D boards are commercially available and have the characteristic of being able to sample at least 8 channels with a sampling frequency of between 500–40,000 samples per second on each channel. An example of such an A/D Board is the National Instruments AT-MIO-16X that is available from National Instruments, Texas, USA. The D/A function is achieved using commercially available 8–21 bit resolution D/A boards. Examples of such a D/A are the National Instruments A/D,D/A Board AT-MIO-16X or National Instruments DSP model AT-DS2200. The radiation driver amplifiers are commercially available, with 2–16 ohms output impedance and an output power of 60–500 watts. An example of such amplifiers is the Inkel amplifier type NA-420, from Inkel of Seoul, Korea. The radiators are also commercially available and have the following characteristics: 1–6 cm radius, 0.5–3 cm thickness, and 100–500 turns made of copper wire of diameter 0.1–0.95 mm. A specific example of such a coil could be coils having a 4 cm radius, 1 cm thickness with 151 turns of copper wire of 0.41 mm diameter.

While the sensor described above is preferred, other sensors may be suitable for some applications, such as Hall effect sensors, for example those available from Allegro Micro Systems, Inc., USA or magneto-resistor sensors, sensors, flux gate magnetic sensors, and/or other magnetic flux sensors.

Controller 40 represents an assemblage of units to perform intended functions. For example, such units may receive information or signals, process information, function as a controller, display information, and/or generate information or signals. Typically controller 40 may comprise one or more microprocessors.

In accordance with a preferred embodiment of the invention, active portion 16 of catheter 10 is a forward looking ultrasound send/receive transducer. Such a transducer can give a one-dimensional map of the acoustic properties of the material lying in front of it by radiating a focused beam of pulsed acoustic energy and then measuring the echoes of the beam reflected by changes in acoustic properties along the path of the beam. In order to provide a three dimensional image it is necessary to change the direction of the beam, preferably without changing its position by a great amount.

In particular, such a steerable, one dimensional acoustic transducer can be used to map the heart walls or blood vessels, ultrasonically, from inside the heart. When coupled with a reference location sensor at a reference point on the heart and ECG gating of the acoustic pulses, such a transducer can generate the information required to form a three dimensional image of the heart or blood vessels or any other organ, at one or several different phases of the heart cycle.

Figure 10A:
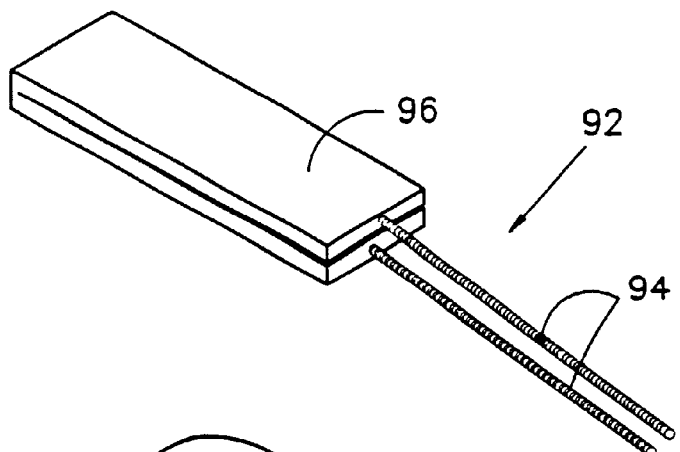
FIGS. 10A–10D illustrate a principle of orienting the tip of a catheter in accordance with a first preferred embodiment of the invention.

The principle of two preferred embodiments of a steering mechanism are shown in FIGS. 10A–10D and 11 respectively. FIG. 10A shows a steering mechanism 92 that fits into the distal end of a catheter and comprises two steering wires 94 attached to a steering head 96. Head 96 is formed of a relatively flexible material such as stainless steel and is slit along its axis, each side of the split being attached to one of wires 94. Such a head may be manufactured by attaching two wires (94) at their end and then flattening the wires to form a more easily bent structure.

Attached to the distal end of the steering head is a relatively rigid housing containing locating sensor 14 and active portion 16 which, in the present preferred embodiment, is an ultrasonic send/receive transducer. At least head 96 and wires 94 are encased in a catheter sheath 104 which is not shown in FIGS. 10A–10C for clarity of presentation. This steering mechanism can also be used for other active portion types such as for electropysiologic mapping procedures and for improved steering of catheters or many types, with or without location sensing.

Figure 10B:
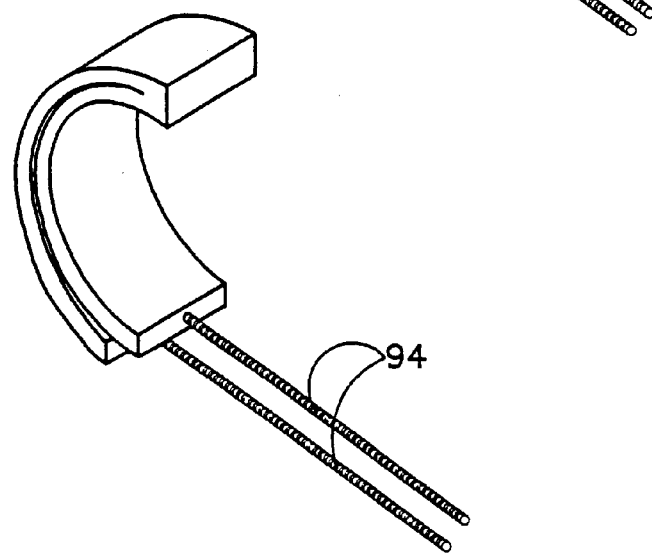
Figure 10C:
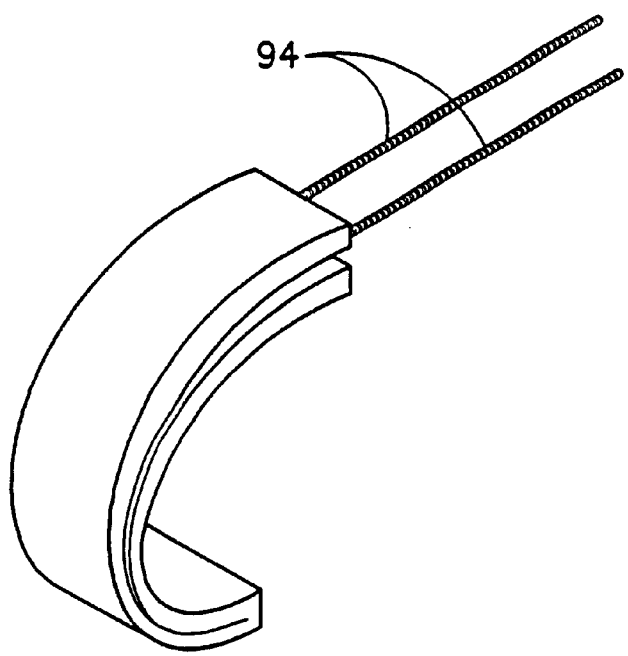

In FIG. 10B one of wires 94 has been shortened as compared with the other wire. Since the catheter sheath holds the wires together, the result of such shortening of one wire is bending of the head, which is facilitated by the axial slit. Locating sensor 14 and active portion 16 are rigidly attached so that measurement of position and orientation of the locating sensor will give the position and orientation of the active portion (ultrasound transducer). By varying the angle of bending and rotating the catheter, imaging over nearly 360° image can be achieved. Additionally or alternatively, as shown in FIG. 10C, the amount of rotation can be reduced by shortening the other wire and which causes bending in the other direction. Slight motion of the transducer can be corrected by a simple translation of the acquired one dimensional image associated with the particular position.

Figure 10D:
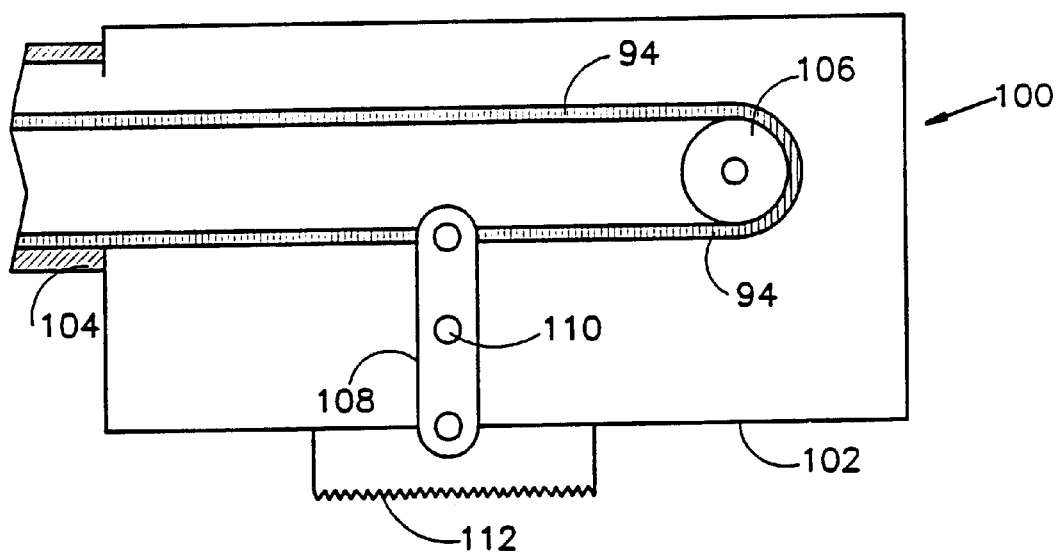

FIG. 10D shows a mechanism 98 placed at the proximal end of the catheter for changing the relative lengths of wires 94. A handle 100 comprises a housing 102 to which catheter sheath 104 is attached. The proximal end of wires 94 are formed in a loop (for example by welding the ends of the wire) and wrapped around a spindle 106 which is preferably fixed and which forms a frictional contact with the wires.

A lever 108 is rotatably attached near its center at a pin 110 to the housing and is attached at one end to wire 94 and at the other end to a slider 112 which is slidable parallel to the housing. When the slider is moved, one of the wires 94 at the distal end is lengthened with respect to the other.

Figure 11:
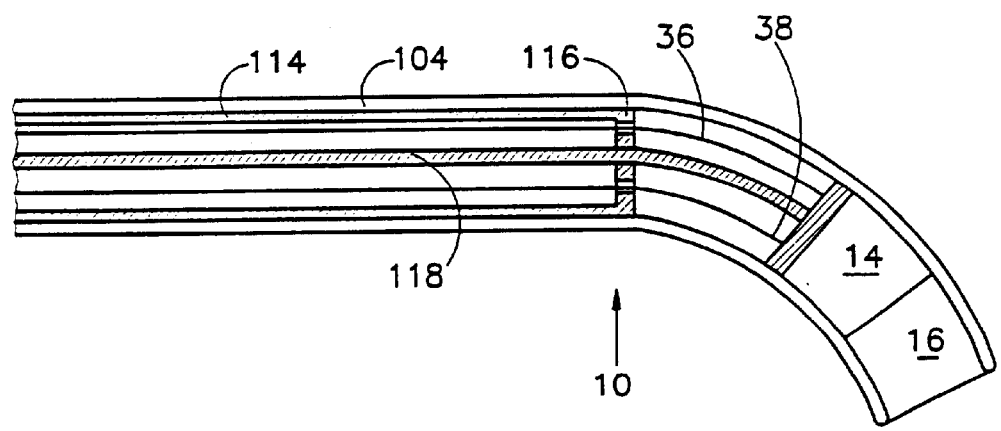
FIG. 11 illustrates a principle of orienting the tip of a catheter in accordance with a second preferred embodiment of the invention.

FIG. 11 shows the distal end of a catheter having an alternative steering mechanism. A relative rigid sleeve 114 is placed within cathode sheath 104. Sleeve 114 can be axially displaced relative to the sheath from the proximal end of the catheter.

The distal end of sleeve 104 is formed with a disk 116 through which a relatively less rigid wire 118 passes. Wire 118 is formed with a permanent bend near its distal end at which end, position sensor 14 and active portion 16 are attached. Axial movement of sleeve 104 straightens wire 118 resulting in a change in orientation of both the position sensor and the active portion. If wire 118 is sited off axis, then rotating the wire will rotate the catheter.

It should be understood that steering of acoustic beams may also be achieved by a moving mirror or by a phased array ultrasonic transducer, and that such a mirror or other arrangement may be present in the active portion. Such active scanning may supplement or replace the passive steering provided by the mechanisms of FIGS. 10 and 11.

Figure 12:
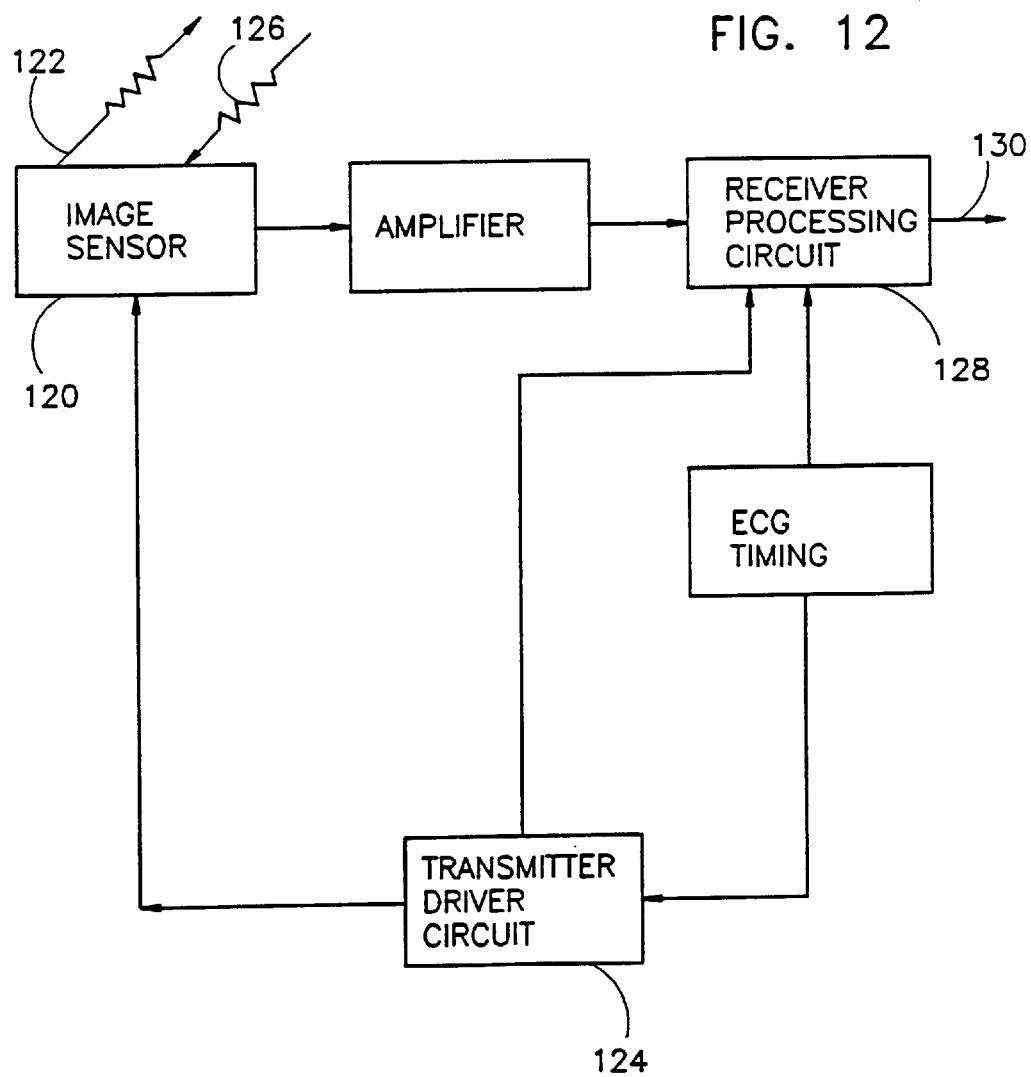
FIG. 12 is a block diagram of ultrasonic acquisition and signal processing circuitry in accordance with a preferred embodiment of the invention.

FIG. 12 shows a simplified system block diagram of ultrasonic acquisition and image formation in accordance with a preferred embodiment of the invention. An image sensor 120, such as the ultrasound sensor described above, transmits an acoustic pulse 122 in response to a signal received from a transmitter-driver circuit 124. An acoustic echo 126 (generally comprising several echoes) is received by the image sensor which produces an echo signal, which when amplified, is sent to a receiver processing circuit 128 which generates a one dimensional "image" at its output 130. Information identifying the heart phase of the image may also be present at output 130 which may comprise a plurality of output ports. In one embodiment of the invention, especially useful for heart imaging, the acquisition of the image is made in response to signals received from an ECG monitor 132. This allows for acquisition of images at a particular portion of the heart cycle so that the various one-dimensional images can be easily reconstructed into a three dimensional image.

In particular, if the most significant echo is used as the measure of the distance from the ultrasonic sensor to the chamber along the measurement direction of the sensor, then the collection of such distances (referenced to a reference point in the chamber) will allow the reconstruction of the surface morphology.

Figure 13:
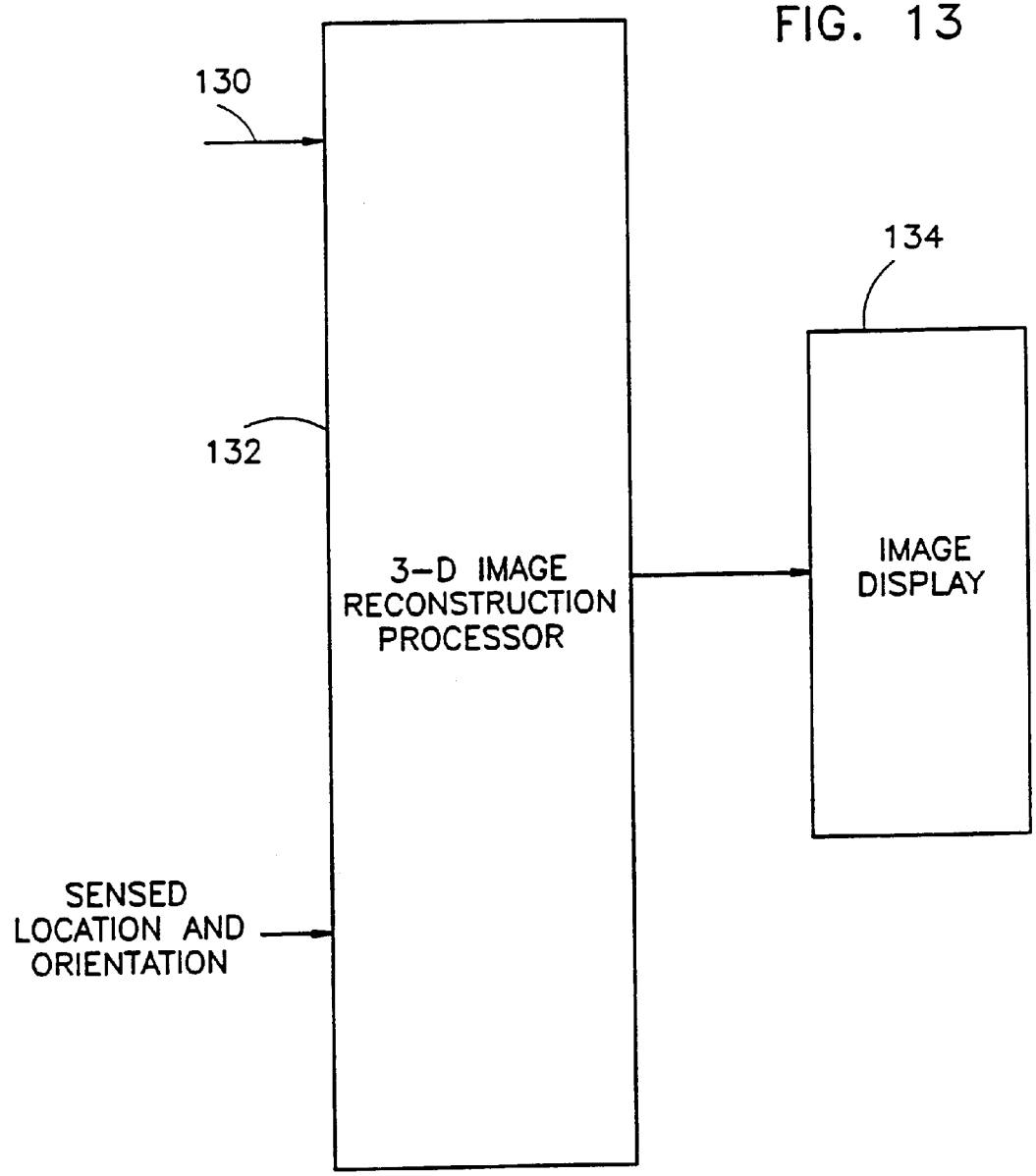
FIG. 13 is a block diagram of image reconstruction circuitry in accordance with a preferred embodiment of the invention.

FIG. 13 shows a simplified block diagram of a three dimensional image reconstruction system which utilizes a series of one dimensional images generated by the circuitry of FIG. 12 and continuous sensed location and orientation information generated by the position locator and its associated circuitry as described above. In general it is useful to acquire the sensed location and orientation to coincide with the acquisition of each one-dimensional image. One of the various methods described above for steering the distal tip of the catheter is used to acquire a plurality of one dimensional images with a plurality of orientations. An automatic mechanism may be used to continuously change the orientation of the imaging head in accordance with the principles of FIGS. 10 and 11 and to rotate the catheter so that operator intervention is not required.

An image reconstruction processor 132 orients and references the individual one dimensional images in accordance with the sensed location and orientation information and forms a 3-D image which can be presented on an image display 13 either in the form of a series of two dimensional slices or a full three dimensional reconstruction. When images at different points in the heart cycle are acquired, the image displayed may be a cine image of the reconstruction.

In a preferred embodiment of the invention a two dimensional image is acquired by the ultrasound sensor which can be a phased array of acoustic crystals of a single crystal in conjunction with a mirror rotating about an axis that deflects the ultrasonic beam in a predetermined path.

In a preferred embodiment of the invention active portion 16 comprises a sensor for sensing electrical signals generated at selectable positions on the heart. As described below, such sensings of electrical signals can be used to map the electrical activity of the heart. The active portion may also include an electrode useful for pacing the heart and/or for ablating a portion of the heart. Such ablation is especially useful in the treatment of the most common lethal cardiac arrhythmia, ventricular tachycardia (VT), i.e., very rapid and ineffectual contractions of the heart muscle. VT is the cause of death of approximately 300,000 people annually. It is also useful in the treatment of other arrhythmias.

Figure 14:
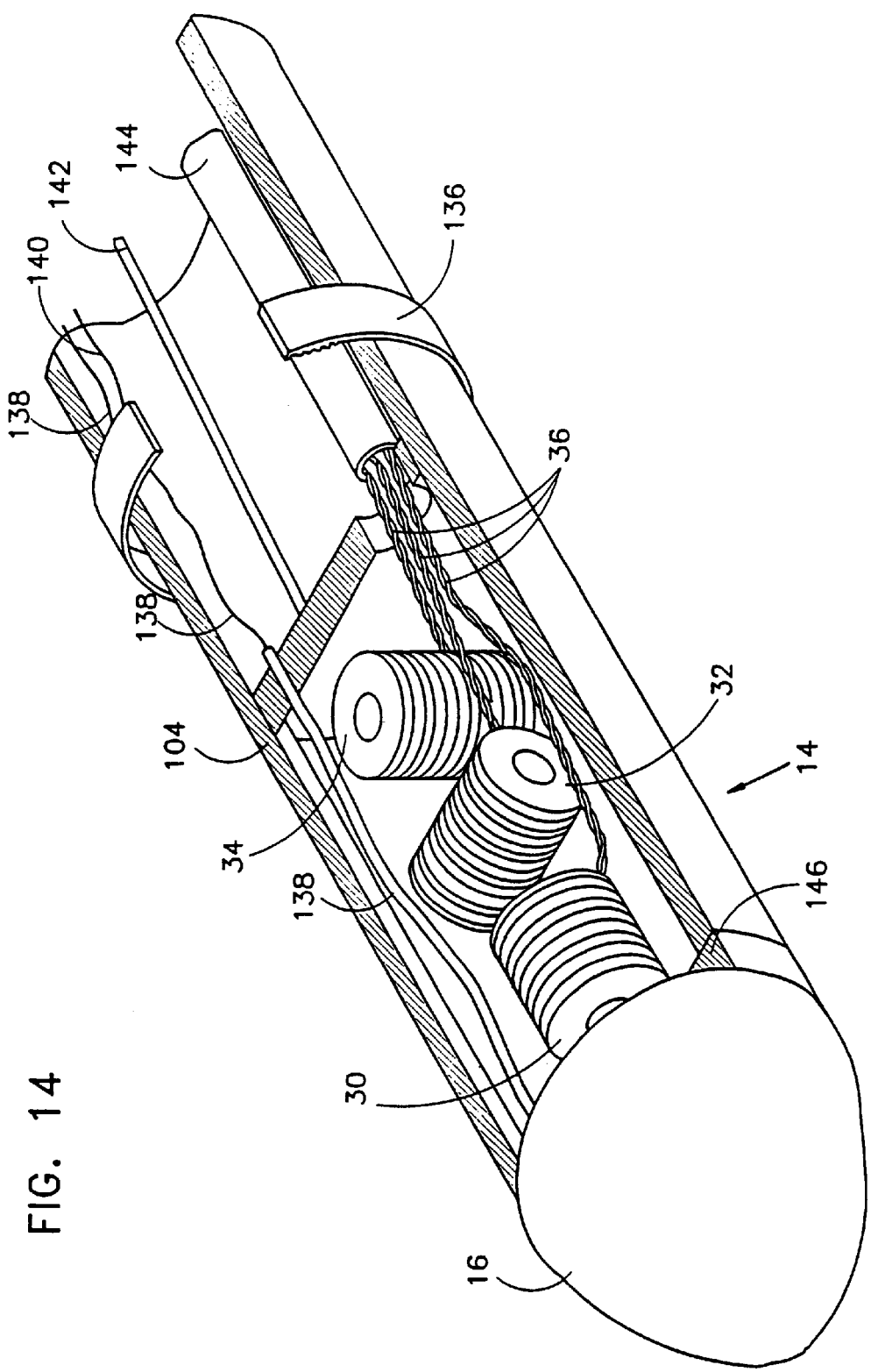
FIG. 14 is a partially schematic, partially cut-away illustration of a probe for electrical sensing, pacing and ablation in accordance with a preferred embodiment of the invention.

A catheter useful for electrical mapping of the heart/ablation is shown schematically in FIG. 14.

Active portion 16 comprises a conducting tip, preferably of platinum, having a length of between 1–12 mm, preferably about 2 mm. The tip is connected via a tip electrode lead-in wire 138 to a switch at the proximal end of the cathode which switches the tip to a source of voltage for pacing or/ablating or to a detector for detecting electrical signals generated by the heart. A conducting ring electrode 136 is placed, proximal to locating sensor 14, on the outside of catheter sheath 104 and is connected to ground or to a recorder via a return lead 140. When used for pacing, as described below, a 1–10 ma pulse is applied between tip 16 and ring electrode 136. When used for ablation RF energy at about 0.5 MHz and 10–100 V is applied for 10–200 sec.

Locating sensor 14 is rigidly attached to the tip and the sensor and tip may be manipulated by an eccentric wire 142. The twisted wire leads are preferably shielded by a shield 144 to reduce pickup from the relatively high voltages carried by leads 138 and 140.

Preferably, an electrically insulating heat shield 146 is placed between the tip and the locating sensor.

Figure 15:
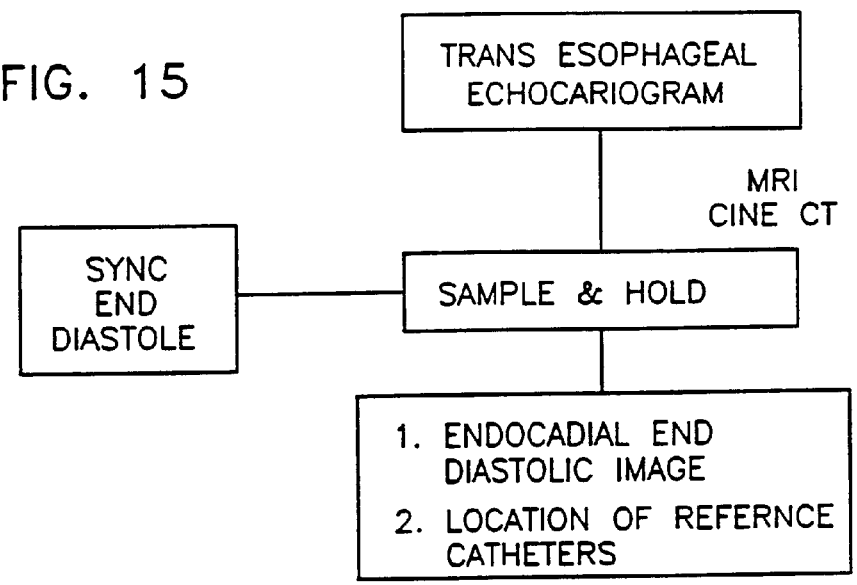
FIG. 15 is a schematic block diagram for acquiring a basic electrogram map in accordance with a preferred embodiment of the present invention.

FIG. 15 is a schematic block diagram for acquiring a basic electrocardiogram map in accordance with a preferred embodiment of the invention. Using a transesophageal echocardiograph in the preferred embodiment, a multiplane image of the heart chambers is acquired prior to the mapping study. The image is acquired only during a fiducial point in time during the cardiac cycle. In the preferred embodiment, the image is acquired at end-diastole in response to an end diastole synch-signal. A three-dimensional image of the heart chambers is reconstructed indicating the endocardial morphology and the location of one or more reference catheters within the heart chamber. This image can be acquired by a 3-D transesophogal ultrasound image, by a CT scanner, by an MRI scanner or by other imaging techniques. The image can also be constructed by touching the catheter to the surface of the chamber (endocardium) in a number of places and measuring the positions. These points can then be used to describe a thee dimensionsional surface which represents the chamber surface.

In the previous PCT and U.S. applications (PCT/US94/08352 filed Jul. 20, 1994 and 08/094,539 respectively), in which fewer than six location and orientation values were determined, reference locatable catheters were place at three positions in the heart to form a reference plane against which the position of the active catheter was referenced.

Preferably, these reference locatable catheters were placed, for example, in the right ventricular apex, the right atrial appendage, and the pulmonary artery at the level of the pulmonary valve, respectively. When a reference catheter having a location sensor 14 as described hereinabove is used for reference purposes, only a single sensor is required to define the relative location and orientation of the mapping catheter. While any of these locations can be used, it is presently preferred to place the reference sensor in the distal coronary sinus.

Figure 16:
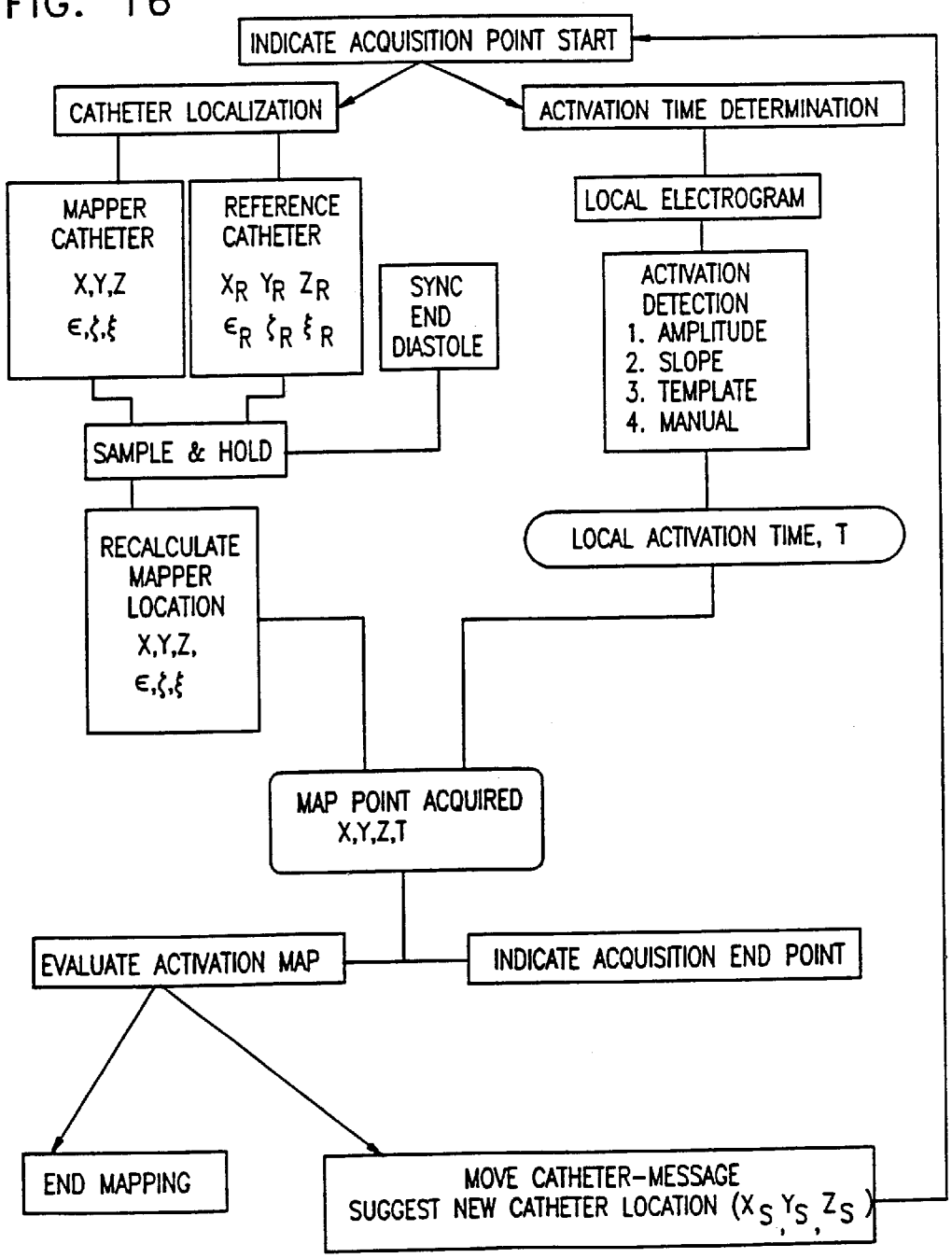
FIG. 16 is a schematic block diagram representing a computerized endocardial mapping algorithm, in accordance with a preferred embodiment of the invention.

FIG. 16 is a schematic block diagram for illustrating the computerized endocardial activation mapping algorithm (used during sinus rhythm mapping and during ventricular tachycardia mapping). A visible or audible indicator preferably indicates the beginning of a data point acquisition. Both electrical activity and location/orientation data are acquired for each point in the map.

The acquisition of catheter location information is shown in left branch of the block diagram of FIG. 16. The mapper electrode is in steady and stable contact with the endocardium. Stable contact is determined by measuring the stability of the location reading, the stability of the sensed electrograms and the impedance of the contact.

The position and orientation of the locating sensor in the mapping catheter are determined continuously in accordance with the method described above and are saved in response to an end diastole synch signal. The mapper catheter tip is localized relative to the reference catheter by finding the difference in each of the six dimensions of the location and orientation. Generally speaking, for the present application the orientation of the mapper cathode is not required, however, it must be acquired to properly transform its location and orientation to an internal heart coordinate system.

Simultaneously, the activation time of the heart at the mapper cathode tip is determined as shown on the right side of FIG. 16. First the local electrocardiogram at the tip of the mapper catheter is acquired and the activation time is calculated based on comparing the amplitude and slope of the local electrocardiogram to a template or manually by the user. The local activation times is then defined with reference to the activation time measured by an ECG terminal on the skin of the patient.

The process of data acquisition can be terminated by the user, or can be evaluated by an "evaluate activation map" algorithm described below, that examines the already acquired activation map for the density of information relative to the spatial gradient of activation times. This algorithm can indicate the next preferable site for activation time detection. The catheter is moved by the user to the new site, and the process of mapping continues.

During VT a data point is determined about every 4 to 6 heart beats. Thus, approximately 15 to 25, typically about 20, data points can be determined each minute.

Figure 17:
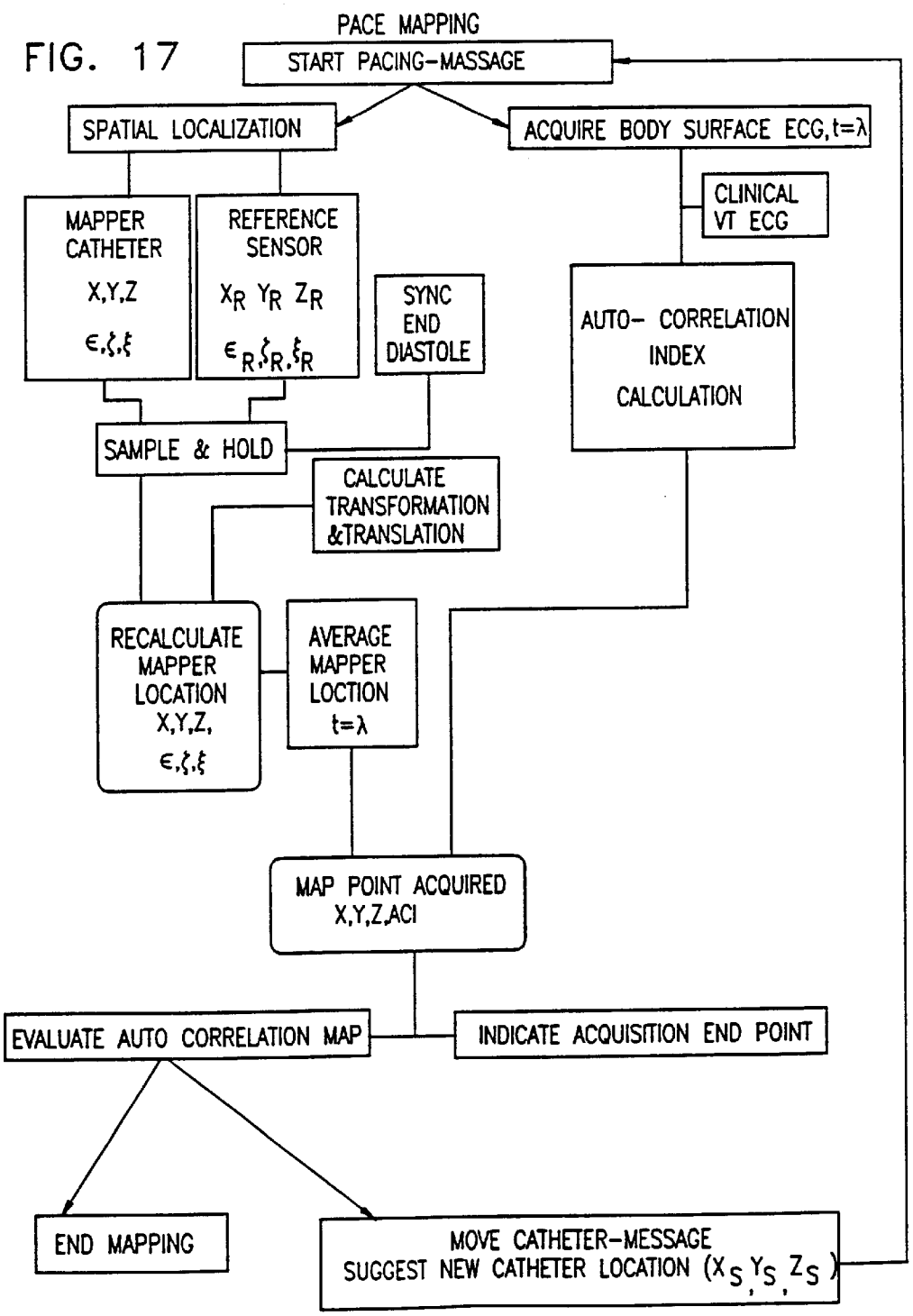
FIG. 17 is a schematic block diagram representing a computerized pace mapping algorithm, in accordance with a preferred embodiment of the invention.

FIG. 17 is a schematic block diagram for illustrating the computerized pace mapping algorithm. A visible or audible indicator indicates the beginning of a data point acquisition. Acquisition of position information is similar to that for FIG. 16 except that the average mapper location in the previous n heartbeats (n is the moving average window duration) is calculated.

The right side of FIG. 17 shows the determination of the ACI (AutoCorelation Index) in a pace mapping mode.

In a "pace mapping mode" an ECG processor acquires ECG data while the patient's heart is paced by an external source at a rate similar to the patient's arrhythmia cycle length. The ECG data is also acquired from the body surface electrograms, and the signals are stored as a segment of ECG with a length of several cycles. The signal acquired is subjected to automatic comparison with the patient's own VT signal (see FIG. 18). The comparison between arrhythmia morphology and paced morphology is performed in two stages: First, the phase shift between the template VT signal and the paced ECG morphology is estimated using minimal error or maximal cross-correlation for two signals. Then, using this phase shift estimated from an index ECG channel, the similarity of the VT and the paced ECG morphology is measured as the average of the cross-correlation or the square error of the two signals of all channels recorded.

This two-stage calculation is repeated each time using a different ECG channel as the index channel for determining the phase shift.

At the end of this procedure the minimal error or the maximal cross-correlation found will be reported to the operator as the ACI of this pacing site.

Figure 18:
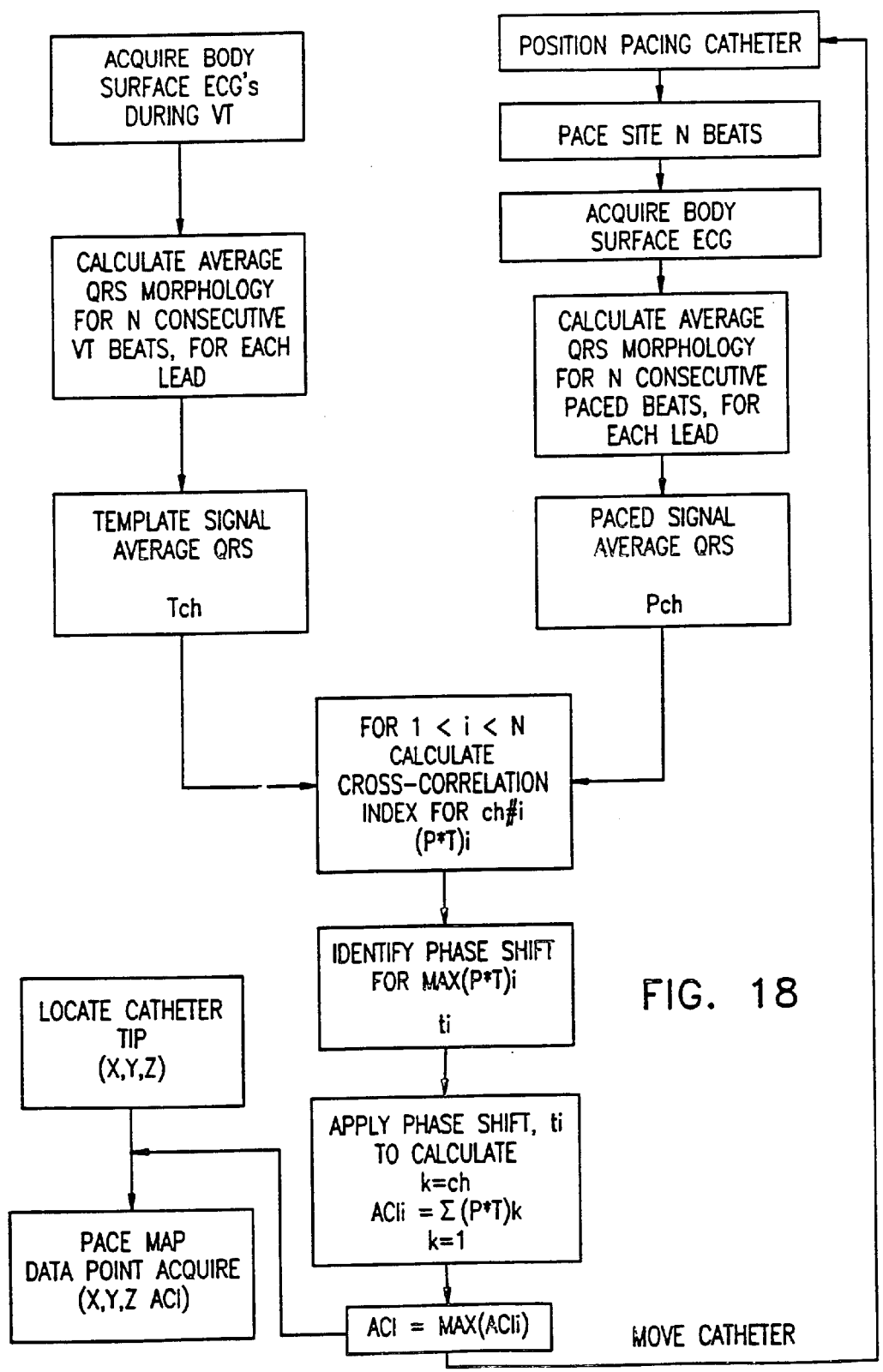
FIG. 18 is a schematic block diagram of an algorithm used to calculate the cross-correlation index while pace-mapping, in accordance with a preferred embodiment of the invention.

FIG. 18 is a schematic block diagram illustrating an algorithm used to calculate the cross-correlation index while pace-mapping in accordance with a preferred embodiment of the invention. Body surface ECG data is acquired at two stages. First, during spontaneous or pacing induced VT, and second, during pacing the endocardium at different sites. The ECG data acquired during VT are signal averaged, and a template is constructed ($T_{ch}$, for each channel recorded). During endocardial pacing the ECG data is acquired, and the same number of beats (N) is acquired to calculate the signal averaged QRS ($P_{ch}$, for each channel recorded). The algorithm then calculates the phase shift between $P_{ch}$ and Tch, which yields for the first channel the maximal cross-correlation. This time shift is used to shift the remaining channels and calculate for them the cross-correlation. All cross-correlations for all channels are summarized and stored. The algorithm then uses the next channel recorded to calculate the time shift that will cause maximal cross-correlation in this channel. Now this time shift is applied for all cross-correlations between $P_{ch}$ and $T_{ch}$, and again all cross-correlations are summarized. This procedure is repeated for all channels, and the maximal cross-correlation achieved is used as the value of the cross-correlation of the $T_{ch}$ and the $P_{ch}$ at this site on the endocardium.

Figure 19:
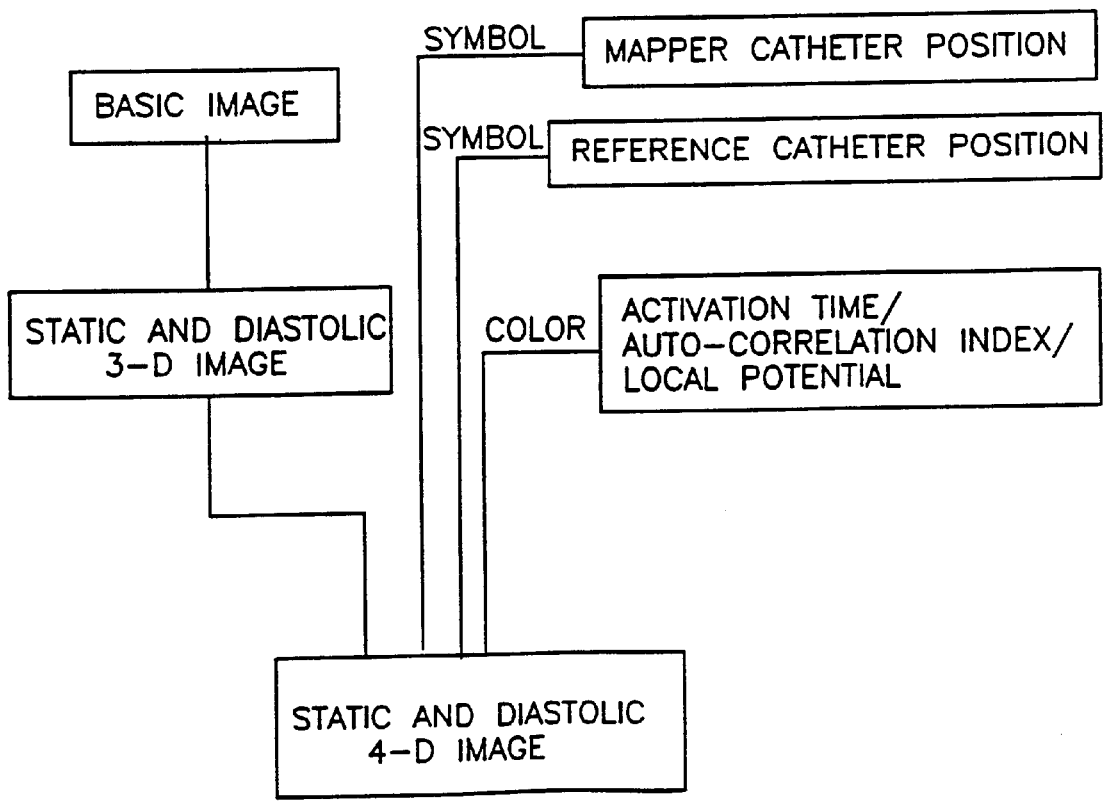
FIG. 19 is a schematic block diagram representing an output configuration of an imaging system in accordance with a preferred embodiment of the invention.

FIG. 19 is a schematic block diagram for illustrating the output configuration of the present embodiment. A quasi-static picture of the heart chambers is presented as 3-D reconstruction of a basic image acquired prior to or during the study as previously described. Superimposed on the image is the location of the mapping/ablation catheter (corrected for the movement of the reference catheter) and the current and previous information acquired from the mapping study. This information may include, when appropriate, the activation times (presented using a color code at each acquisition site) or cross-correlation index (ACI) for each point in the pace map. Furthermore, the map can represent in the color coding the duration of the local electrograms, the presence of fragmented activity as well as various other variables calculated by the electrophysiologic processor.

The above principles can be applied for mapping other structures of the body, for example, of the urinary bladder, brain, or gastrointestinal tract. Dependent upon the examination technique, the catheter may be replaced by a needle whose tip is the locatable sensor port.

At each stage (sinus rhythm mapping, pace mapping and VT mapping) after each data point is acquired, all available information is reassessed for two purposes: first, to suggest to the operator the next site for data acquisition, and second, to test the available information to propose a site for ablation.

Two algorithms are running simultaneously to perform this procedure:

(1) Mapping guidance algorithm. This algorithm uses as an input the available mapped information of a certain variable (e.g., local activation time during sinus rhythm). The algorithm calculates the spatial derivative of the mapped variable (i.e., activation time in this example) and calculates the next best location for adding another data point when the objective function is regularizing the spatial gradients of the mapped variable. For example, this algorithm will suggest that more data points be acquired in areas in which the mapped variable is changing significantly over a short distance.

The location suggested by the algorithm is be presented to the operator as a symbol on the display. The same display already shows the basic image of the heart chamber and the current location of the mapping/ablation catheter. Therefore, the operator will move the mapping/ablation catheter to reach the suggested location for further data acquisition.

This algorithm is most beneficial during VT mapping, where the available time for data acquisition is limited by the adverse hemodynamic effects of the arrhythmia. Therefore, such an algorithm which examines the available data points of a map in real-time and immediately suggests the next site for acquisition is very useful.

(2) Prognosing likelihood of successful ablation algorithm. This algorithm is a user-defined set of hierarchical rules for evaluating the acquired information such as the rules given immediately below. The operator is expected to grade the importance of the specific information acquired in the mapping/ablation procedure, as to its likelihood to identify the correct site for ablation.

Grading of mapping results suggesting the likelihood of successful ablation at that site (A=highly likely successful and D=least likely successful):

(a) The identification of a typical re-entrant pathway on VT mapping with an identifiable common slow pathway—Grade A;
(b) The identification of a site with over 90% correlation index in the pace map—Grade B;
(c) The identification of a site where VT was terminated with a non-capture premature stimulus—Grade C; and
(d) The identification of pre-potential maps recorded during VT, which are similar to diastolic potential maps recorded during sinus rhythm—Grade D.

Other types of electrographic maps of the heart are also possible. By use of variables determined from paced or non-paced acquisitions of electrographic data, the following additional maps can be generated:

(1) Sinus rhythm activation map (isochronal map);
(2) Diastolic potential occurrence time map
(3) Local latency isochronal map during pace mapping;
(4) Activation time isochronal map during VT; and
(5) Pre-potential isochronal map during VT mapping.

Also, the sites where VT was terminated by a non-captured premature stimulus can be presented.

The acquisition of these maps and of other factors suitable for mapping and procedures for their determination as well as additional details of the above mapping procedures can be found in the above mentioned U.S. patent application Ser. No. 08/094,539 and PCT Application PCT/US94/08352.

What is claimed is:

1. A locating system for determining the location and orientation of an invasive medical instrument having a distal end relative to a reference frame, comprising:

a plurality of field generators which generate known, distinguishable fields in response to drive signals, wherein the field generated by each field generator has a different frequency and each said different frequency is an integer multiple of a given frequency;

an invasive medical instrument;

a locating sensor having at least one coil situated in the invasive medical instrument near the distal end thereof which generate at least one sensor signal in response to said fields; and a signal processor which has an input for a plurality of signals corresponding to said drive signals and said at least one sensor signal and which computes location coordinates and orientation coordinates of a portion of the invasive medical instrument, responsive to said drive and said at least one sensor signal.

2. The locating system according to claim 1 wherein the plurality of field generators comprise three distinguishable, non-overlapping generators.

3. The locating system of claim 1 wherein said plurality of field generators have a plurality of coils which have axes which intersect within a coil.

4. The locating system of claim 1 wherein said at least one coil comprises three coils and wherein said three coils have axes which do not all intersect in a point.

5. The locating system of claim 1 wherein the fields generated by each of the field generators have a different phase.

6. The locating system of claim 1 wherein the fields are AC magnetic fields.

7. The locating system of claim 6, wherein the AC magnetic fields are continuous fields.

8. The locating system of claim 1 and including a display system for displaying the position of a point on the invasive medical instrument.

9. The locating system of claim 1 wherein there is an additional sensor on a portion of the invasive medical instrument which senses a local condition.

10. The locating system of claim 9 wherein the additional sensor senses local electrical signals and transfers them to terminals external to a patient's body.

11. The locating system of claim 10, wherein the signals are electrical signals from the endocardium of the patient's heart.

12. The locating system of claim 11, wherein the signal processor processes position and orientation coordinate signals and the local electrical signals acquired at a plurality of points on the endocardium by the locating sensor and the additional sensor respectively of the medical instrument to generate a map that represents the propagation of electrical signals through tissue in the patient's body.

13. The locating system of claim 9 wherein the portion of the invasive medical instrument includes an ablator for supplying electrical energy to the endocardium for ablating a portion of the endocardium.

14. The locating system of claim 9 wherein the additional sensor is an ultrasonic transmitter/receiver.

15. The locating system of claim 14 wherein the ultrasonic transmitter/receiver provides a less than three dimensional representation of the acoustic properties of tissue beyond the distal end.

16. The locating system according to claim 15 wherein the portion is a distal end of the invasive medical instrument, wherein the distal end is deflectable.

17. The locating system according to claim 16 and including image reconstruction circuitry which receives a plurality of said less than three dimensional representations acquired at different orientations of the distal end and produces a three dimensional map of the acoustic properties of tissue at least partially surrounding the distal end.

18. The locating system of claim 1 and including an electrode adapted for supplying electrical energy to the endocardium for ablating a portion of the endocardium.

19. The locating system of claim 1 and further comprising a reference instrument which includes a plurality of sensors situated in the reference instrument, and a display system, wherein said display system displays the position of a point on the invasive medical instrument relative to the position of a point on the reference instrument.

20. The locating system of claim 19, further comprising a single reference instrument.

21. The locating system of claim 19 wherein the reference instrument is an invasive medical instrument and wherein said sensors are situated proximate the distal end thereof.

22. The system of claim 1 wherein the invasive medical instrument is a catheter or endoscope.

23. A method of determining the position and orientation of an invasive medical instrument having a distal end, comprising:
   (a) generating a plurality of distinguishable, geometrically different AC magnetic fields such that the AC magnetic fields are generated at a different frequency wherein each different frequency in an integer multiple of a given frequency;
   (b) sensing the AC magnetic fields at a plurality of sensors proximate the distal end; and
   (c) computing six dimensions of position and orientation of a portion of the invasive medical instrument responsive to signals representative of the generated magnetic fields and the sensed magnetic fields.

24. A method according to claim 23 wherein the AC magnetic fields are sensed at three points of the invasive medical instrument.

25. A locating system for determining the location and orientation of an invasive medical instrument having a distal end relative to a reference frame, comprising:
   a plurality of field generators which generate known, distinguishable fields in response to drive signals wherein the field generated by each field generator has a different frequency and each said different frequency is an integer multiple of a given frequency;
   a plurality of sensors situated in the invasive medical instrument proximate the distal end thereof which generate sensor signals in response to said fields; and
   a signal processor which has an input for a plurality of signals corresponding to said drive signals and said sensor signals and which computes three location coordinates and three orientation coordinates of a portion of the invasive medical instrument, responsive to said drive and sensor signals.

26. The locating system of claim 25, wherein the signal processor cross-correlates the signals corresponding to the drive and sensor signals to provide cross-correlation results.

27. The locating system of claim 26 wherein the signal processor uses the results of the cross-correlation to calculate the contribution of each field generator to the signal generated by each said sensor.

28. The locating system of claim 25, wherein the signal processor cross-correlates the signals corresponding to the drive and sensor signals and wherein the duration of the cross-correlation of the inputs is the minimal common product of the integer multipliers divided by the given frequency.

* * * * *